(12) United States Patent
Jandrot-Perrus et al.

(10) Patent No.: US 8,466,258 B2
(45) Date of Patent: Jun. 18, 2013

(54) POLYPEPTIDES, CYCLIC POLYPEPTIDES AND PHARMACEUTICAL COMPRISING THEREOF FOR NON INVASIVE SPECIFIC IMAGING OF FIBROSIS

(75) Inventors: Martine Jandrot-Perrus, Paris Cedex (FR); Julien Muzard, Paris (FR); Philippe Billiald, Paris Cedex (FR); Dominique le Guludec, Paris Cedex (FR); Laure Sarda, Paris Cedex (FR); Alain Meulemans, Paris Cedex (FR)

(73) Assignees: INSERM (Institut National de la Santé et de la Recherche Médicale), Paris (FR); Universite Paris Diderot—Paris 7, Paris (FR)

( * ) Notice: Subject to any disclaimer, the term of this patent is extended or adjusted under 35 U.S.C. 154(b) by 344 days.

(21) Appl. No.: 12/746,996

(22) PCT Filed: Dec. 11, 2008

(86) PCT No.: PCT/EP2008/067275
§ 371 (c)(1),
(2), (4) Date: Aug. 17, 2010

(87) PCT Pub. No.: WO2009/074628
PCT Pub. Date: Jun. 18, 2009

(65) Prior Publication Data
US 2010/0303724 A1    Dec. 2, 2010

(51) Int. Cl.
*C07K 4/00* (2006.01)
*C07K 7/00* (2006.01)
*C07K 7/64* (2006.01)
*C07K 14/00* (2006.01)
*C07H 21/02* (2006.01)
*A61K 49/00* (2006.01)
*C12N 15/00* (2006.01)
*C12N 5/00* (2006.01)

(52) U.S. Cl.
USPC ........... 530/300; 530/317; 530/326; 530/327; 536/23.1; 435/320.1; 435/325; 424/9.1

(58) Field of Classification Search
None
See application file for complete search history.

(56) References Cited

FOREIGN PATENT DOCUMENTS
WO     01/16321      3/2001
WO   2006/054904     5/2006

OTHER PUBLICATIONS

International Search Report in PCT/EP08/67275, dated Mar. 11, 2009.
Caravan et al., Angewandte Chemie, 46(43):8171-8173 (2007).
van den Borne et al., Circulation, 116(16):289-290 (2007).
Jandrot-Perrus et al., Blood, 104(11):433 (2004).

*Primary Examiner* — Christina Bradley
*Assistant Examiner* — Lianko Garyu
(74) *Attorney, Agent, or Firm* — McAndrews, Held & Malloy, Ltd.

(57) ABSTRACT

The present invention relates to diagnostic imaging and in particular to the diagnostic imaging of fibrosis. More particularly, the present invention provides a polypeptides, cyclic polypeptides and pharmaceutical compositions suitable for the non-invasive visualization of fibrosis. The polypeptide of the invention may comprise an amino acid sequence consisting of: X1-X2-M-H-G-L-X7-L-X9-X10-D-E (SEQ ID NO: 1) wherein amino acid X1 is R, F or P; amino acid X2 is F or V; amino acid X7 is Q, H or L; amino acid X9 is W or G and amino acid X10 is A or D.

20 Claims, 10 Drawing Sheets

A

B

Figure 1:
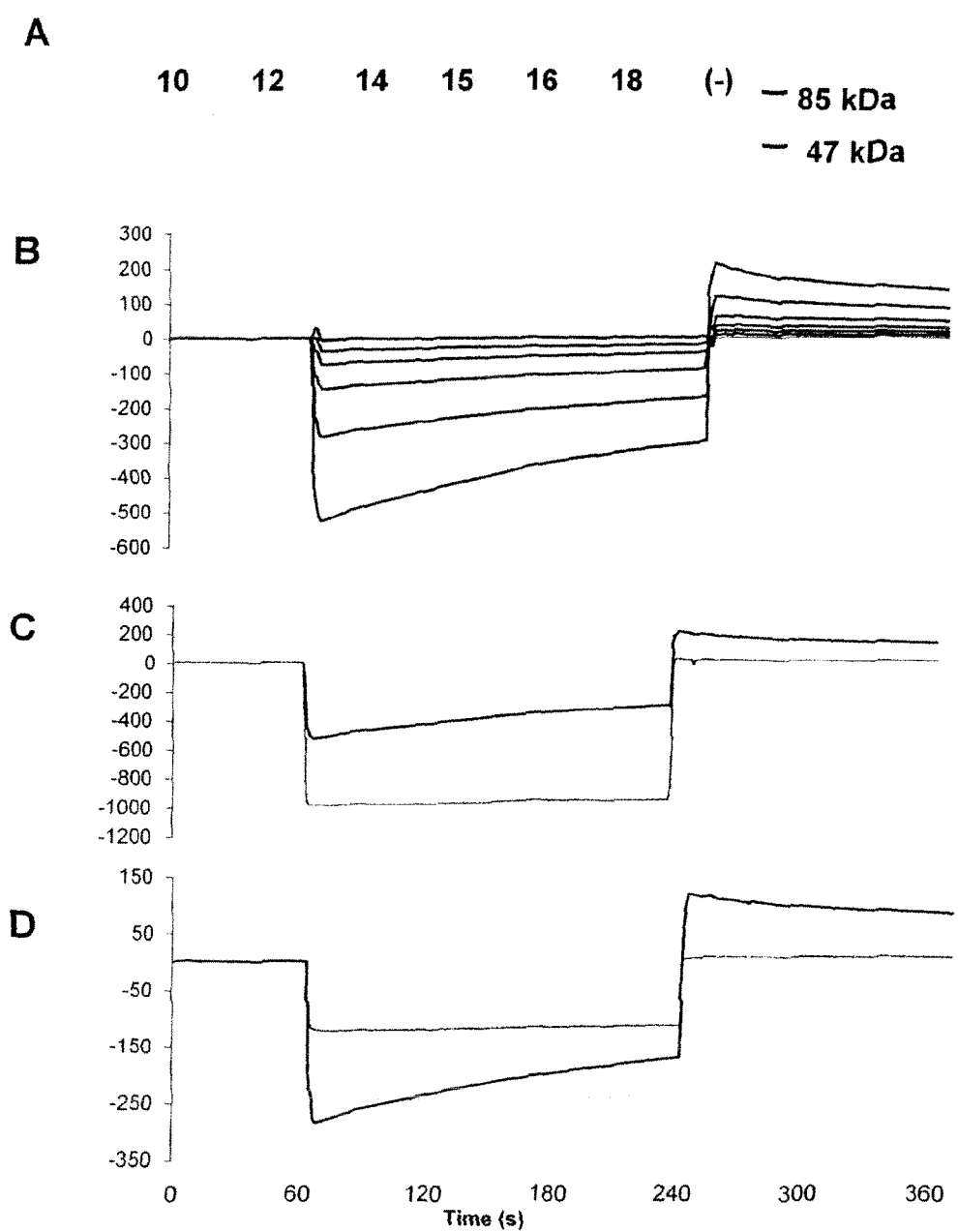

Pulmonary fibrosis  Control mouse  *Pulmonary fibrosis*
99mTc-B-Collagelin scintigraphy  *99mTc-Pc*

99mTc-B-Collagelin

Pulmonary fibrosis  Control mouse

99mTc- collagelin

Bleomycin-treated  control

99mTc- Pc

Bleomycin-treated  control

Bleomycin-treated mice

Tc99m-B-Collagelin

Sirius red    Autoradiography        Sirius red    Autoradiography

Tc99m-B-Pc

Sirius red    Autoradiography

POLYPEPTIDES, CYCLIC POLYPEPTIDES AND PHARMACEUTICAL COMPRISING THEREOF FOR NON INVASIVE SPECIFIC IMAGING OF FIBROSIS

FIELD OF THE INVENTION

The present invention relates to diagnostic imaging and in particular to the diagnostic imaging of fibrosis. More particularly, the present invention provides polypeptides, cyclic polypeptides and pharmaceutical compositions which specifically target collagen and are suitable for the non-invasive specific imaging of fibrosis.

BACKGROUND OF THE INVENTION

Fibrosis is defined pathologically as inappropriate repair by connective tissue and is caused by increased synthesis and decreased degradation of matrix proteins, most notably collagen types I and III.

Fibrosis can affect virtually every tissue and organ system. Excessive fibrosis following physical, thermal, metabolic, ischemic, infectious, inflammatory, or immunological injury can occur in any part of the body, and can cause destruction of the affected structures such as lung, kidney, heart, liver, vascular system, skin, eye, bone marrow. Fibrotic tissue is characterized by a loss of normal architecture, paucity of stromal cells, and replacement of blood vessels and other essential parenchymal structures by dense, homogeneous, and increasingly stable extracellular matrix.

Fibrosis is increasingly recognized as an important feature of many chronic diseases, and as such, represents an enormous health burden. The United States government estimates that 45% of deaths in the United States can be attributed to conditions associated with fibrosis.

For example, fibrotic liver disease ranks as the eighth most common cause of mortality worldwide, accounting for 1.3 million deaths annually (Murray and Lopez, 1997, Lancet 349, 1269-1276). The cellular mechanisms of fibrosis are complex. In response to liver injury, for example caused by chronic hepatitis C virus (HCV) infection, hepatitis B virus (HBV) infection, alcoholic or fatty liver disease, drug-induced liver disease or primary biliary cirrhosis, normally quiescent hepatic stellate cells are activated into proliferating myofibroblasts. As a result, fibrosis may accumulate through increased production of tissue and proteins like collagen and decreased degradation of these compounds so that the function of liver is impaired. Especially in viral chronic hepatitis, early detection of fibrosis would be clinically relevant for therapeutical decision making since the occurrence of fibrosis represents a major poor prognostic factor.

Another example concerns atherosclerosis, which is significantly associated with aging. Atherosclerotic plaques are rich in type I collagen. When the plaque is vulnerable, collagen becomes exposed to the blood flow and triggers arterial thrombosis and ischemia of downstream tissues. Non invasive molecular imaging of vulnerable atherosclerotic lesions attracts much interest to identify patients at risk for thromboischemic vascular event. For example, a recent study evaluates the feasibility of radiolabeled soluble Glycoprotein VI (GPVI) agent for non-invasive imaging of vulnerable atherosclerotic plaques.

In diabetes mellitus, early detection of diabetic cardiomyopathy which comprises intersticial fibrosis would be of clinical interest for early identification of diabetic patients at risk for heart failure. Also in idiopathic dilated cardiomyopathy, fibrosis is recognized as a major prognostic factor.

Several biomarkers have been searched for diagnosing fibrosis, but very few methods have been developed for the in vivo visualization of fibrosis in an organ. For example, recent studies show that transient echography or MRI elastography represents methods to assess liver fibrosis by measuring non invasively liver stiffness in adult patients (de Ledinghen V. et al. 2007; Talwalkar J A et al. 2007). Also, preliminary experiences were done with diffusion-weighted MRI for quantification of liver fibrosis (Taouli B et al, AJR Am J Roentgenol 2007; 189 (4): 799-806).

Some attempts to image myocardial fibrosis were performed with gadolinium delayed-enhanced MRI (Tzelepis G E et al, Arthritis Rheum 2007; 56 (11):3827-36). But these techniques are not specific for fibrosis. Also they may suffer from a lack of sensitivity since large amounts of fibrosis are necessary to impair tissue elasticity. Specific imaging tracers for molecular imaging of fibrosis represents a challenge and a large field of interest for different imaging modalities including radionuclide imaging and MRI (collagen-targeted MRI contrast agent for molecular imaging of fibrosis, Caravan P et al, Angew Chem Int Ed Engl 2007; 46 (43): 8171-73). Compared to MRI, specific radionuclide imaging has the advantages of higher sensitivity and no toxicity since very low tracer dose (pico or nanomolar) is sufficient to obtain accurate target-to-background ratio.

SUMMARY OF THE INVENTION

The invention relates to a polypeptide comprising an amino acid sequence consisting of:

```
X1-X2-M-H-G-L-X7-L-X9-X10-D-E     (SEQ ID NO: 1)
``` wherein
amino acid X1 is R, F or P;
amino acid X2 is F or V;
amino acid X7 is Q, H or L;
amino acid X9 is W or G and
amino acid X10 is A or D.

The invention also relates to a cyclic polypeptide wherein the polypeptide according to the invention is cyclised via a disulfide bound between two cysteine residues.

The invention also relates to an imaging agent comprising a labelled polypeptide or a cyclic labelled polypeptide according to the invention.

DETAILED DESCRIPTION OF THE INVENTION

An object of the invention relates to a polypeptide comprising an amino acid sequence consisting of:

```
X1-X2-M-H-G-L-X7-L-X9-X10-D-E     (SEQ ID NO: 1)
``` wherein
amino acid X1 is R, F or P;
amino acid X2 is F or V;
amino acid X7 is Q, H or L;
amino acid X9 is W or G and
amino acid X10 is A or D.

It should be recalled that in the description as a whole, "amino acid" is understood to mean the amino acids in the L form which can be found in natural proteins, that is to say alanine (A), arginine (R), asparagine (N), aspartic acid (D), cysteine (C), glutamine (Q), glutamic acid (E), glycine (G), histidine (H), isoleucine (I), leucine (L), lysine (K), methionine (M), phenylalanine (F), proline (P), serine (S), threonine (T), tryptophan (W), tyrosine (Y) and valine (V). However, the present invention also relates to the non-natural amino acids, that is to say the preceding amino acids in their D form, as well as the homo forms of some amino acids such as arginine, lysine, phenylalanine and serine or the nor forms of leucine or valine.

In a particular embodiment, the polypeptide of the invention comprises an amino acid sequence selected from the group consisting of RVMHGLHLGDDE (SEQ ID NO:2); RFMHGLQLWADE (SEQ ID NO:3); RVMHGLQLWADE (SEQ ID NO:4); RVMHGLHLWDDE (SEQ ID NO:5); RVMHGLQLWDDE (SEQ ID NO:6); RVMHGLHLWADE (SEQ ID NO:7); FVMHGLHLGDDE (SEQ ID NO:8); PVMHGLHLWDDE (SEQ ID NO:9); and RVMHGLLLGADE (SEQ ID NO:10).

In a particular embodiment, polypeptides of the invention can be conformationally constrained to enable the polypeptides to bind collagen with a better affinity.

Cyclization is well known in the art and generally involves the introduction of a disulfide bound between two cysteine residues. Typically, the cycle is formed through a side chain to side chain ring involving a monosulfide or disulfide bridge between pairs of cysteines, penicillamines, homocysteines, combinations of the foregoing, or other pairs of amino acids in which the side chains are linked with either one or two sulfur atoms. Methods for the synthesis of disulfide cyclic polypeptide are well known in the art and are described for example in U.S. Pat. No. 3,929,758, U.S. Pat. No. 4,216,141; and U.S. Pat. No. 4,102,877.

Polypeptides of the invention may thus comprise cysteine residues at terminal ends to allow the cyclisation of the polypeptides. In a particular embodiment, the cysteine residues are separated from the terminal ends of the polypeptide of the invention by 1, 2, 3 or more amino acids. Typically, the amino acids are selected in a manner that they do not prevent the collagen binding of the polypeptides. The amino acids may preferably be selected among small and neutral amino acids such as Glycine or Proline. Proline could structurally favour cyclisation. In another particular embodiment, the polypeptides of the invention may comprise tripeptides flanking the terminal ends of the polypeptide and comprising at least one cysteine residue. In a particular embodiment, the polypeptide of the invention may comprise a CGP tripeptide at its N-terminal end and a GPC tripeptide at its C-terminal end.

Accordingly, polypeptides of the invention may comprise an amino acid sequence consisting of:

```
CGP-X1-X2-MHGL-X7-L-X9-X10-DE-GPC   (SEQ ID NO: 11)
``` wherein
amino acid X1 is R, F or P;
amino acid X2 is F or V;
amino acid X7 is Q, H or L;
amino acid X9 is W or G and
amino acid X10 is A or D.

In another particular embodiment, polypeptides of the invention may comprise an amino acid sequence selected from the groups consisting of

```
CGPRVMHGLHLGDDEGPC;    (SEQ ID NO: 12)

CGPRFMHGLQLWADEGPC;    (SEQ ID NO: 13)

CGPRVMHGLQLWADEGPC;    (SEQ ID NO: 14)
```

```
CGPRVMHGLHLWDDEGPC;    (SEQ ID NO: 15)

CGPRVMHGLQLWDDEGPC;    (SEQ ID NO: 16)

CGPRVMHGLHLWADEGPC;    (SEQ ID NO: 17)

CGPFVMHGLHLGDDEGPC;    (SEQ ID NO: 18)

CGPPVMHGLHLWDDEGPC;    (SEQ ID NO: 19)
and

CGPRVMHGLLLGADEGPC.    (SEQ ID NO: 20)
```

In another particular embodiment, the polypeptides as above described are cyclised via a disulfide bound between the two cysteine residues of the polypeptides.

In another particular embodiment, the invention relates to a cyclic polypeptide having the formula:

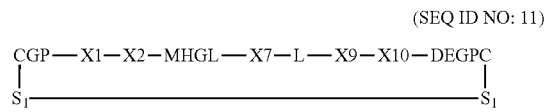

(SEQ ID NO: 11)

wherein
$S_1$ is sulfur;
amino acid X1 is R, F or P;
amino acid X2 is F or V;
amino acid X7 is Q, H or L;
amino acid X9 is W or G and amino acid X10 is A or D.

In another particular embodiment, the invention further relates to a cyclic polypeptide having the formula:

(SEQ ID NO: 11)

wherein $S_1$ is sulfur.

In another particular embodiment, the invention further relates to a cyclic polypeptide having the formula:

(SEQ ID NO: 11)

wherein $S_1$ is sulfur.

In another particular embodiment, the invention further relates to a cyclic polypeptide having the formula:

(SEQ ID NO: 11)

wherein $S_1$ is sulfur.

In another particular embodiment, the invention further relates to a cyclic polypeptide having the formula:

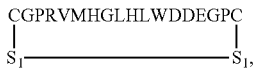 (SEQ ID NO: 11)

CGPRVMHGLHLWDDEGPC
|                 |
S₁────────────────S₁, wherein S₁ is sulfur.

In another particular embodiment, the invention further relates to a cyclic polypeptide having the formula:

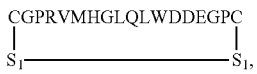 (SEQ ID NO: 11)

CGPRVMHGLQLWDDEGPC
|                 |
S₁────────────────S₁, wherein S₁ is sulfur.

In another particular embodiment, the invention further relates to a cyclic polypeptide having the formula:

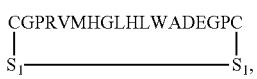 (SEQ ID NO: 11)

CGPRVMHGLHLWADEGPC
|                 |
S₁────────────────S₁, wherein S₁ is sulfur.

In another particular embodiment, the invention further relates to a cyclic polypeptide having the formula:

 (SEQ ID NO: 11)

CGPFVMHGLHLGDDEGPC
|                 |
S₁────────────────S₁, wherein S₁ is sulfur.

In another particular embodiment, the invention further relates to a cyclic polypeptide having the formula:

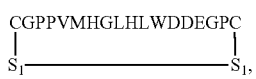 (SEQ ID NO: 11)

CGPPVMHGLHLWDDEGPC
|                 |
S₁────────────────S₁, wherein S₁ is sulfur.

In another particular embodiment, the invention further relates to a cyclic polypeptide having the formula:

 (SEQ ID NO: 11)

CGPRVMHGLLLGADEGPC
|                 |
S₁────────────────S₁, wherein S₁ is sulfur.

Other methods of cyclization are contemplated by the invention. For example, those methods include but are not limited by those described by Marlowe (1993, Biorg. Med. Chem. Lett. 3:437-44) who describes peptide cyclization on TFA resin using trimethylsilyl (TMSE) ester as an orthogonal protecting group; Pallin and Tam (1995, J. Chem. Soc. Chem. Comm. 2021-2022) who describe the cyclization of unprotected peptides in aqueous solution by oxime formation; Algin et al (1994, Tetrahedron Lett. 35:9633-9636) who disclose solid-phase synthesis of head-to-tail cyclic peptides via lysine side-chain anchoring; Kates et al (1993, Tetrahedron Lett. 34:1549-1552) who describe the production of head-to-tail cyclic peptides by three-dimensional solid phase strategy; Tumelty et al (1994, J. Chem. Soc. Chem. Comm. 1067-1068) who describe the synthesis of cyclic peptides from an immobilized activated intermediate, wherein activation of the immobilized peptide is carried out with N-protecting group intact and subsequent removal leading to cyclization; McMurray et al (1994, Peptide Res. 7:195-206) who disclose head-to-tail cyclization of peptides attached to insoluble supports by means of the side chains of aspartic and glutamic acid; Hruby et al (1994, Reactive Polymers 22:231-241) who teach an alternate method for cyclizing peptides via solid supports; and Schmidt and Langer (1997, J. Peptide Res. 49:67-73) and those described by Davies J S (The cyclisation of peptides and depsipeptides J Pept Sci 2003, 8:471-501); and Li and Roller (PPCyclisation strategies in peptide derived drug design. Curr. Tp Med. Chem. 2002, 3:325-41.).

In another particular embodiment, polypeptides or cyclic polypeptides of the invention may comprise a spacer sequence at its terminal ends. Such spacer sequence may be suitable to label said polypeptide or cyclic polypeptide of the invention with a detectable substance (e.g., biotin moiety). Actually, the spacer sequence may be useful to prevent the steric hindrance of the detectable substance. For example, the spacer sequence for biotin may consist in a SGSG amino acid sequence that may be attached to the N-terminal end of the polypeptide or cyclic polypeptide of the invention.

In a particular embodiment, the polypeptides of the invention may comprise an amino acid sequence consisting of:

(SEQ ID NO: 21)
SGSGCGP-X1-X2-MHGL-X7-L-X9-X10-DE-GPC wherein amino acid X1 is R, F or P;

amino acid X2 is F or V;

amino acid X7 is Q, H or L;

amino acid X9 is W or G and amino acid X10 is A or D.

In another particular embodiment, the polypeptides of the invention may comprise an amino acid sequence selected from the groups consisting of

| | |
|---|---|
| SGSGCGPRVMHGLHLGDDEGPC; | (SEQ ID NO: 22) |
| SGSGCGPRFMHGLQLWADEGPC; | (SEQ ID NO: 23) |
| SGSGCGPRVMHGLQLWADEGPC; | (SEQ ID NO: 24) |
| SGSGCGPRVMHGLHLWDDEGPC; | (SEQ ID NO: 25) |
| SGSGCGPRVMHGLQLWDDEGPC; | (SEQ ID NO: 26) |
| SGSGCGPRVMHGLHLWADEGPC; | (SEQ ID NO: 27) |
| SGSGCGPFVMHGLHLGDDEGPC; | (SEQ ID NO: 28) |
| SGSGCGPPVMHGLHLWDDEGPC; and | (SEQ ID NO: 29) |
| SGSGCGPRVMHGLLLGADEGPC. | (SEQ ID NO: 30) |

In another particular embodiment, the invention relates to a cyclic polypeptide having the formula:

(SEQ ID NO: 21)

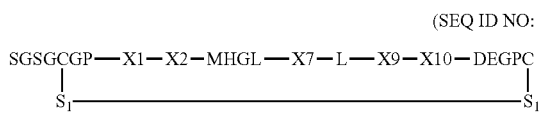

wherein

S₁ is sulfur;

amino acid X1 is R, F or P;

amino acid X2 is F or V;

amino acid X7 is Q, H or L;

amino acid X9 is W or G and amino acid X10 is A or D.

In another particular embodiment, the invention further relates to a cyclic polypeptide having the formula:

(SEQ ID NO: 21)

wherein S₁ is sulfur.

The following constrained peptide SGSGCPGRVMHGLHLGDDEGPC is named "collagelin".

In another particular embodiment, the invention further relates to a cyclic polypeptide having the formula:

(SEQ ID NO: 21)

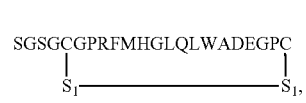

wherein S₁ is sulfur.

In another particular embodiment, the invention further relates to a cyclic polypeptide having the formula:

(SEQ ID NO: 21)

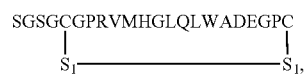

wherein S₁ is sulfur.

In another particular embodiment, the invention further relates to a cyclic polypeptide having the formula:

(SEQ ID NO: 21)

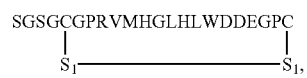

wherein S₁ is sulfur.

In another particular embodiment, the invention further relates to a cyclic polypeptide having the formula:

(SEQ ID NO: 21)

wherein S₁ is sulfur.

In another particular embodiment, the invention further relates to a cyclic polypeptide having the formula:

(SEQ ID NO: 21)

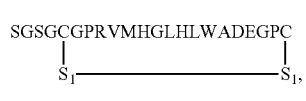

wherein S₁ is sulfur.

In another particular embodiment, the invention further relates to a cyclic polypeptide having the formula:

(SEQ ID NO: 21)

wherein S₁ is sulfur.

In another particular embodiment, the invention further relates to a cyclic polypeptide having the formula:

(SEQ ID NO: 21)

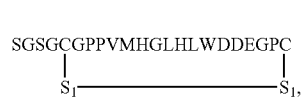

wherein S₁ is sulfur.

In another particular embodiment, the invention further relates to a cyclic polypeptide having the formula:

(SEQ ID NO: 21)

wherein S₁ is sulfur.

In another embodiment, the polypeptides of the invention are PEGylated. It has been widely demonstrated that the conjugation of polyethylene glycol PEG to peptides significantly increases their duration of biological activity (half-life). PEG provides a more stable conformation and increases the size and the weight of the molecule, thereby prolonging the circulation time of the peptide.

Polyethylene glycol (PEG) is formed by a process of linking repeating units of ethylene glycol to form polymers with linear or branched shapes of different molecular mass. PEG is an hydrophilic, biocompatible and non-toxic water-soluble polymer of general formula HO—(CH2-CH2-O)n-H, wherein n>4. Its molecular weight varies from 300 to 40,000 Daltons.

PEGylation of the polypeptide of the invention may be accomplished by known methods in the art. For example, polyethylene glycol may be attached to the protein either directly or by an intervening linker.

One non limitative way of proceeding is to bound covalently polyethylene glycol through amino acid residues via a reactive group, such as, a free amino or carboxyl group. Linkerless systems for attaching polyethylene glycol to proteins are described in Delgado et al., Crit. Rev. Thera. Drug Carrier Sys. 9:249-304 (1992), Francis et al., Inter J. of Hematol. 68:1-18 (1998), U.S. Pat. No. 4,002,531, U.S. Pat. No. 5,349,052, WO 95/06058 and WO 98/32466.

One system for attaching polyethylene glycol directly to amino acid residues of proteins without an intervening linker employs tresylated MPEG, which is produced by the modification of monomethoxy polyethylene glycol (MPEG) using tresylchloride. Upon reaction of protein with tresylated MPEG, polyethylene glycol is directly attached to amine groups of the protein. Thus, the invention includes protein-polyethylene glycol conjugates produced by reacting proteins of the invention with a polyethylene glycol molecule having a 2,2,2-trifluoreothane sulphonyl group.

Polyethylene glycol can also be attached to proteins using a number of different intervening linkers. For example, U.S. Pat. No. 5,612,460 discloses urethane linkers for connecting polyethylene glycol to proteins. Protein-polyethylene glycol conjugates wherein the polyethylene glycol is attached to the protein by a linker can also be produced by reaction of proteins with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional polyethylene glycol derivatives and reaction chemistries for attaching polyethylene glycol to proteins are described in WO 98/32466.

The number of polyethylene glycol moieties attached to each polypeptide (i.e., the degree of substitution) may also vary. For example, the pegylated proteins of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per protein molecule. Methods for determining the degree of substitution are discussed, for example, in Delgado et al., Crit. Rev. Thera. Drug Carrier Sys. 9:249-304 (1992).

In another embodiment of the invention, the polypeptides of the invention are oligomerized, preferably dimerized.

Oligomerization is widely described in the scientific literature and constits in a specific assembly of monomeric polypeptides to form a stable polymere.

Oligomerization increases the size and the weight of biological activity, thereby prolonging the circulation time (half-life) of the peptide.

In a particular embodiment, the N and C terminal ends of the polypeptides and cyclic polypeptides of the invention may be protected by any well known method in the art. For example, carboxyl function at the C-terminal end of the polypeptides and cyclic polypeptides of the invention may be substituted by an amide.

The polypeptides of the invention may be produced by any technique known per se in the art, such as, without limitation, any chemical, biological, genetic or enzymatic technique, either alone or in combination.

Knowing the amino acid sequence of the desired sequence, one skilled in the art can readily produce said polypeptides, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions.

Alternatively, the polypeptides of the invention can be synthesized by recombinant DNA techniques as it is now well-known in the art. For example, these fragments can be obtained as DNA expression products after incorporation of DNA sequences encoding the desired (poly)peptide into expression vectors and introduction of such vectors into suitable eukaryotic or prokaryotic hosts that will express the desired polypeptide, from which they can be later isolated using well-known techniques.

Therefore, a further object of the invention relates to an isolated nucleic acid molecule encoding for a polypeptide of the invention.

Typically, said nucleic acid molecule is a DNA or RNA molecule, which may be included in any suitable vector, such as a plasmid, cosmid, episome, artificial chromosome, phage or a viral vector. The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence.

So, a further object of the invention relates to a vector comprising a nucleic acid molecule of the invention.

Such vectors may comprise regulatory elements, such as a promoter, enhancer, terminator and the like, to cause or direct expression of said polypeptide upon administration to a subject. The vectors may further comprise one or several origins of replication and/or selectable markers. The promoter region may be homologous or heterologous with respect to the coding sequence, and provide for ubiquitous, constitutive, regulated and/or tissue specific expression, in any appropriate host cell, including for in vivo use. Examples of promoters include bacterial promoters (T7, pTAC, Trp promoter, etc.), viral promoters (LTR, TK, CMV-IE, etc.), mammalian gene promoters (albumin, PGK, etc), and the like.

Examples of plasmids include replicating plasmids comprising an origin of replication, or integrative plasmids, such as for instance pUC, pcDNA, pBR, and the like. Examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. No. 5,882,877, U.S. Pat. No. 6,013,516, U.S. Pat. No. 4,861,719, U.S. Pat. No. 5,278,056 and WO 94/19478.

A further object of the present invention relates to a cell which has been transfected, infected or transformed by a nucleic acid and/or a vector according to the invention. The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed".

The nucleic acids of the invention may be used to produce a recombinant polypeptide of the invention in a suitable expression system. The term "expression system" means a host cell and compatible vector under suitable conditions, e.g. for the expression of a protein coded for by foreign DNA carried by the vector and introduced to the host cell.

Common expression systems include *E. coli* host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include *E. coli, Kluyveromyces* or *Saccharomyces* yeasts, and mammalian cell lines (e.g., Vero cells, CHO cells, 3T3 cells, COS cells, etc.).

The present invention also relates to a method for producing a recombinant host cell expressing a polypeptide according to the invention, said method comprising the steps consisting of: (i) introducing in vitro or ex vivo a recombinant nucleic acid or a vector as described above into a competent host cell, (ii) culturing in vitro or ex vivo the recombinant host cell obtained and (iii), optionally, selecting the cells which express and optionally secrete said polypeptide. Such recombinant host cells can be used for the production of the polypeptides according to the present invention, as previously described.

The invention further relates to a method of producing a polypeptide of the invention, which method comprises the steps consisting of: (i) culturing a transformed host cell according to the invention under conditions suitable to allow expression of said polypeptide; and (ii) recovering the expressed polypeptide.

Polypeptides of the invention may be used in an isolated (e.g., purified) form or contained in a vector, such as a membrane or lipid vesicle (e.g. a liposome).

In a preferred embodiment, polypeptides or cyclic polypeptides of the invention may be labelled with a detectable molecule or substance, such as a fluorescent molecule, a radioactive molecule or any others labels known in the art. Labels are known in the art that generally provide (either directly or indirectly) a signal.

As used herein, the term "labeled", with regard to the polypeptide or cyclic polypeptide of the invention, is intended to encompass direct labeling of the polypeptide or cyclic polypeptide of the invention by coupling (i.e., physically linking) a detectable substance.

Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin.

The detectable substance may be a radioactive metal ion, i.e. a radiometal. Suitable radiometals can be either positron emitters such as $^{64}Cu$, $^{48}V$, $^{52}Fe$, $^{55}Co$, $^{94m}Tc$ or $^{68}Ga$; gamma-emitters such as $^{99m}Tc$ $^{111}In$ $^{113m}In$ or $^{67}Ga$ or beta-emitters such as $^{67}Cu$, $^{89}Sr$, $^{90}Y$, $^{153}Sm$, $^{136}Re$, $^{188}Re$ or $^{192}Ir$.

In this particular embodiment polyamino polycarboxylate chelators such as diethylenetriaminepentaacetic acid (DTPA) or 1,4,7,10-tetraazacyclododecane-N,N',N'',N'''-tetraacetic acid (DOTA) were also developed for labeling radiometals. These chelators allow labeling with radioisotopes suitable for imaging such as $^{111}In$ for single photon emission computed tomography (SPECT) and $^{68}Ga$ for positron emission tomography (PET). Polyamino polycarboxylates are also suitable chelators for $^{90}Y$ and $^{177}Lu$ isotopes.

The detectable substance may be a paramagnetic metal ion, suitable such metal ions include: Gd(III), Mn(II), Cu(II), Cr(III), Fe(III), Co(II)1 Er(II)1 Ni(II), Eu(III) or Dy(III).

The detectable substance may be a gamma-emitting radioactive halogen. The radiohalogen is suitably chosen from $^{123}I$, $^{131}I$ or $^{77}Br$.

The detectable substance may be a positron-emitting radioactive non-metal. Suitable such positron emitters include: $^{11}C$, $^{23}N$, $^{15}O$, $^{17}F$, $^{18}F$, $^{75}Br$, $^{76}Br$ or $^{124}I$.

The detectable substance may be a hyperpolarised NMR-active nucleus. Such NMR-active nuclei may have a non-zero nuclear spin, and include $^{13}C$, $^{15}N$, $^{19}F$, $^{29}Si$ and $^{31}P$. By the term "hyperpolarised" is meant enhancement of the degree of polarisation of the NMR-active nucleus over its' equilibrium polarisation. The natural abundance of $^{13}C$ (relative to $^{12}C$) is about 1%, and suitable $^{13}C$-labelled compounds are suitably enriched to an abundance of at least 5%, preferably at least 50%, most preferably at least 90% before being hyperpolarised. At least one carbon atom of the imaging agent of the invention is suitably enriched with $^{13}C$, which is subsequently hyperpolarised.

The detectable substance may be a reporter suitable for in vivo optical imaging, the reporter is any moiety capable of detection either directly or indirectly in an optical imaging procedure. The reporter might be a light scatterer (e.g. a coloured or uncoloured particle), a light absorber or a light emitter. More preferably the reporter is a dye such as a chromophore or a fluorescent compound. The dye can be any dye that interacts with light in the electromagnetic spectrum with wavelengths from the ultraviolet light to the near infrared. Most preferably the reporter has fluorescent properties.

Preferred organic chromophoric and fluorophoric reporters include groups having an extensive delocalized electron system, e.g. cyanines, merocyanines, indocyanines, phthalocyanines, naphthalocyanines, triphenylmethines, porphyrins, pyrilium dyes, thiapyrilium dyes, squarylium dyes, croconium dyes, azulenium dyes, indoanilines, benzophenoxazinium dyes, benzothiaphenothiazinium dyes, anthraquinones, napthoquinones, indathrenes, phthaloylacridones, trisphenoquinones, azo dyes, intramolecular and intermolecular charge-transfer dyes and dye complexes, tropones, tetrazines, b/s(dithiolene) complexes, bistbenzene-dithiolatei complexes, iodoaniline dyes, b/s(S,O-dithiolene) complexes. Fluorescent proteins, such as green fluorescent protein (GFP) and modifications of GFP that have different absorption/emission properties are also useful. Complexes of certain rare earth metals (e.g., europium, samarium, terbium or dysprosium) are used in certain contexts, as are fluorescent nanocrystals (quantum dots).

Particular examples of chromophores which may be used include: fluorescein, sulforhodamine 101 (Texas Red), rhodamine B, rhodamine 6G, rhodamine 19, indocyanine green, Cy2, Cy3, Cy3.5, Cy5, Cy5.5, Cy7, Marina Blue, Pacific Blue, Oregon Green 88, Oregon Green 514, tetramethylrhodamine, and Alexa Fluor 350, Alexa Fluor 430, Alexa Fluor 532, Alexa Fluor 546, Alexa Fluor 555, Alexa Fluor 568, Alexa Fluor 594, Alexa Fluor 633, Alexa Fluor 647, Alexa Fluor 660, Alexa Fluor 680, Alexa Fluor 700, and Alexa Fluor 750.

Particularly preferred are dyes which have absorption maxima in the visible or near infrared (NIR) region, between 400 nm and 3 μm, particularly between 600 and 1300 nm. Optical imaging modalities and measurement techniques include, but not limited to: luminescence imaging; endoscopy; fluorescence endoscopy; optical coherence tomography, transmittance imaging; time resolved transmittance imaging; confocal imaging; nonlinear microscopy; photoacoustic imaging; acousto-optical imaging; spectroscopy; reflectance spectroscopy; interferometry; coherence interferometry; diffuse optical tomography and fluorescence mediated diffuse optical tomography (continuous wave, time domain and frequency domain systems), and measurement of light scattering, absorption, polarisation, luminescence, fluorescence lifetime, quantum yield, and quenching.

Preferred detectable substances are those which can be detected externally in a non-invasive manner following administration in vivo. Most preferred imaging moieties are radioactive, especially radioactive metal ions, gamma-emitting radioactive halogens and positron-emitting radioactive non-metals, particularly those suitable for imaging using Single photon emission computed tomography (SPECT) or Positron Emission Tomography (PET).

In a further additional aspect, an object of the invention relates to the use of a labelled polypeptide or cyclic polypeptide of the invention as an imaging agent.

The term "imaging agent" refers to a compound designed to target fibrosis in a mammal, and which can be detected following its administration to the mammalian body in vivo.

In another further aspect, the present invention relates to an imaging agent which comprises a labelled polypeptide or cyclic polypeptide of the invention.

In another further aspect, the present invention provides a pharmaceutical composition comprising the imaging agent as described above, together with a biocompatible carrier, in a form suitable for mammalian administration. In a preferred embodiment, the pharmaceutical composition is a radiopharmaceutical composition.

The "biocompatible carrier" is a fluid, especially a liquid, in which the imaging agent is suspended or dissolved, such that the composition is physiologically tolerable, i.e. can be administered to the mammalian body without toxicity or undue discomfort. The biocompatible carrier medium is suitably an injectable carrier liquid such as sterile water for injection; an aqueous solution such as saline; an aqueous solution of one or more tonicity-adjusting substances (e.g. salts of plasma cations with biocompatible counterions), sugars (e.g. glucose or sucrose), sugar alcohols (e.g. sorbitol or mannitol), glycols (e.g. glycerol), or other non-ionic polyol materials (e.g. polyethyleneglycols, propylene glycols and the like).

In an additional aspect, the present invention provides kits for the preparation of the pharmaceutical compositions of the invention. Such kits comprise a labelled polypeptide or cyclic polypeptide of the invention, Hence, the reaction medium for reconstitution of such kits is preferably a "biocompatible carrier" as defined above, and is most preferably aqueous. Suitable kit containers comprise a sealed container which permits maintenance of sterile integrity and/or radioactive safety, plus optionally an inert headspace gas (e.g. nitrogen or argon), whilst permitting addition and withdrawal of solutions by syringe.

The kits may optionally further comprise additional components such as a radioprotectant, antimicrobial preservative, pH-adjusting agent or filler.

By the term "radioprotectant" is meant a compound which inhibits degradation reactions, such as redox processes, by trapping highly-reactive free radicals, such as oxygen-containing free radicals arising from the radiolysis of water. The radioprotectants of the present invention are suitably chosen from: ascorbic acid, para-aminobenzoic acid (i.e. 4-aminobenzoic acid), gentisic acid (i.e. 2,5-dihydroxybenzoic acid) and salts thereof with a biocompatible cation. The "biocompatible cation" and preferred embodiments thereof are as described above.

The imaging agent or pharmaceutical composition of the invention is useful for in vivo imaging of fibrosis. Accordingly, in a yet further aspect, the present invention provides an imaging agent or a pharmaceutical composition of the invention for use in an in vivo diagnostic or imaging method, e.g. SPECT or PET. Preferably said method relates to the in vivo diagnostic or imaging of a condition associated with fibrosis such as lung fibrosis, liver kidney fibrosis, heart fibrosis, vascular system fibrosis, skin fibrosis, eye fibrosis, bone and bone marrow fibrosis. In a particular embodiment, the imaging agent or pharmaceutical composition of the invention are suitable for the in vivo imaging of atherosclerosis and myocardial infarcts, diabetic and idiopathic cardiomyopathy.

This aspect of the invention also provides a method for the in vivo diagnosis or imaging in a patient of a condition associated with fibrosis comprising prior administration of the pharmaceutical composition of the invention. According to the invention, the term "patient", is intended for a human or non-human mammal affected or likely to be affected with fibrosis. Said patient is preferably a mammal and most preferably a human. By "previously administered" is meant that the step involving the clinician, wherein the pharmaceutical is given to the patient e.g., intravenous injection, has already been carried out.

Alternatively, the invention provides a method for imaging a condition associated with fibrosis in a patient comprising the steps consisting of:

a) providing an imaging agent or a pharmaceutical composition according to the invention b) administering said patient with said imaging agent or pharmaceutical agent c) detecting said imaging agent in said patient Another aspect of the invention also encompasses use of the imaging agent of the invention for the manufacture of pharmaceutical composition for the diagnostic imaging in vivo of a condition associated with fibrosis.

Another aspect of the invention relates to the use of the imaging agent as a specific tool for direct targeting of collagen in vitro and in vivo.

The invention will further be illustrated in view of the following figures and examples.

FIGURES

FIG. 1: Immunoblotting of 9O12.2 binding bacterial clones. A: Isolated bacterial clones were lysed and proteins were separated by electrophoresis in non-reducing conditions and analysed by immunoblot using the 9O12.2 IgGs. A positive band of Mr~63 kDa corresponding to the expected mass of the FliTrx™ fusion protein was observed indicating that peptide presented by these clones bound to 9O12.2. Results are shown for six selected clones (extracts from clones 13, 14, 15, 16, 17, 18 and for a negative control performed with the lysate of a clone obtained from the same library but using an irrelevant antibody. B-C Surface plasmon resonance (SPR) analysis of collagelin binding to 9O12.2. The peptide corresponding to the sequence expressed by clone 14 (collagelin) was synthesized coupled to biotin and was immobilized onto a streptavidin coated sensorchip (mean of 20 RU). In B, increasing concentration of the 9O12.2 IgGs were flowed on the sensorchip (0, 1.25, 2.5, 5 and 10 µg/ml). Representative sensorgrams are shown after deduction of non-specific background from a control flow cell coated with an irrelevant peptide. C: Immobilized biotin-collagelin was reduced on the sensorchip using DTT. The 9O12.2 IgG (8 µg/ml) was injected on the sensorchip (black sensorgram) and did not bind to the reduced peptide as compared to non reduced peptide (grey sensorgram). D: 9O12.2 IgG (5 µg/ml) was injected on immobilized biotin-collagelin in the presence of recombinant soluble GPVI (25 µg/ml) (grey sensorgram) that completely inhibited the binding of the IgGs to the peptide when compared to control conditions (black sensorgram). Recombinant GPVI did not bind to the immobilized peptide (light grey sensorgram).

Figure 2:
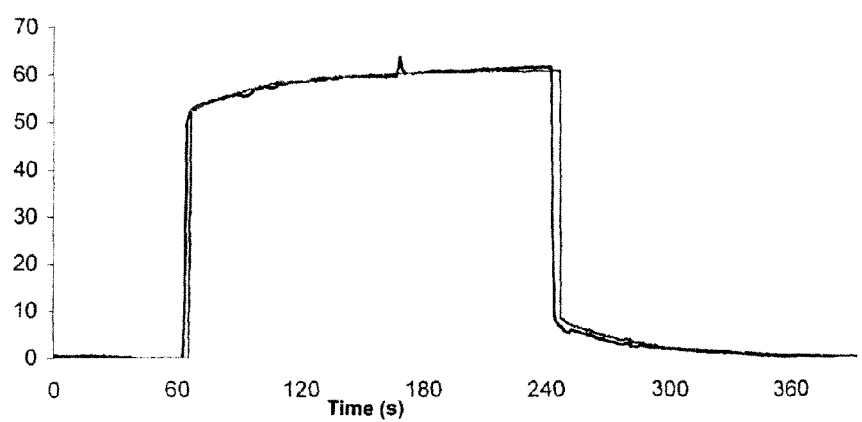
Figure 2:
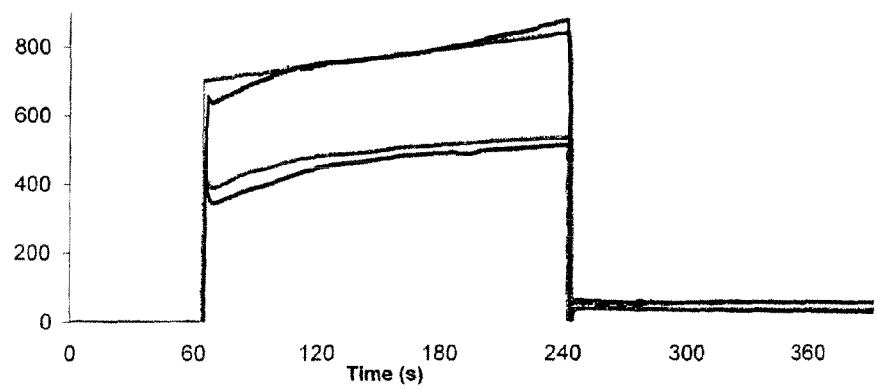

FIG. 2: Interaction of the collagelin with collagen: A Collagen was injected on biotin-collagelin immobilized on a streptavidin coated sensorchip. ~10 RU collagen were bound onto the collagelin coated surface (dark). The fit is also indicated (grey). Non-specific background signal from a control flow cell coated with an irrelevant peptide was deduced. B Binding of collagelin to immobilized collagen. Increasing quantities of biotin-collagelin (250, 500 µg·mL-1) were injected on a collagen immobilized on a CM5 sensorchip. Sensorgrams and interaction fits obtained with the peptide are shown in black and grey respectively. Non-specific background measured using an irrelevant peptide was deduced.

Figure 3:
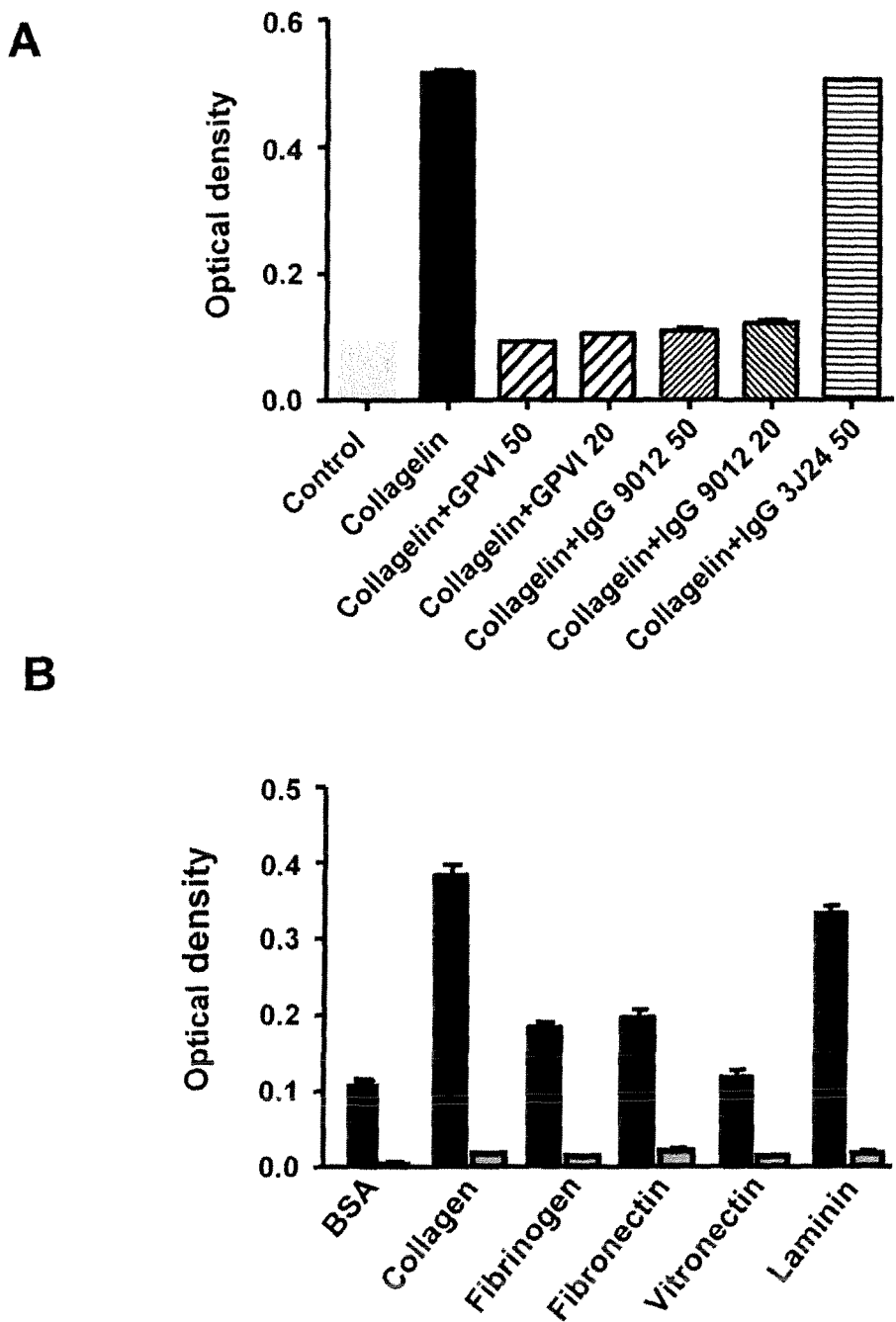

FIG. 3: Peptide Interaction with collagen and with different macromolecules: A Binding of collagelin to immobilized collagen in microtitration plates. biotin-collagelin or control peptide were incubated with immobilized fibrillar type I collagen and bound peptide was detected using peroxydase-coupled extravidine. In competition experiments collagelin was mixed with recombinant soluble GPVI (50 and 20 µg·mL-1), 9O12 IgGs (50 and 20 µg·mL-1) or 3J24.2 IgGs (50 µg·mL-1) prior to addition to collagen-coated wells. B: Binding of biotin-collagelin or control peptide (50 µg·mL-1) to immobilized fibrinogen, fibronectin, vitronectin and laminin. Coating of microtitration wells with the different proteins was performed as with collagen. Bound peptides were detected using peroxidase coupled extravidine.

Figure 4:
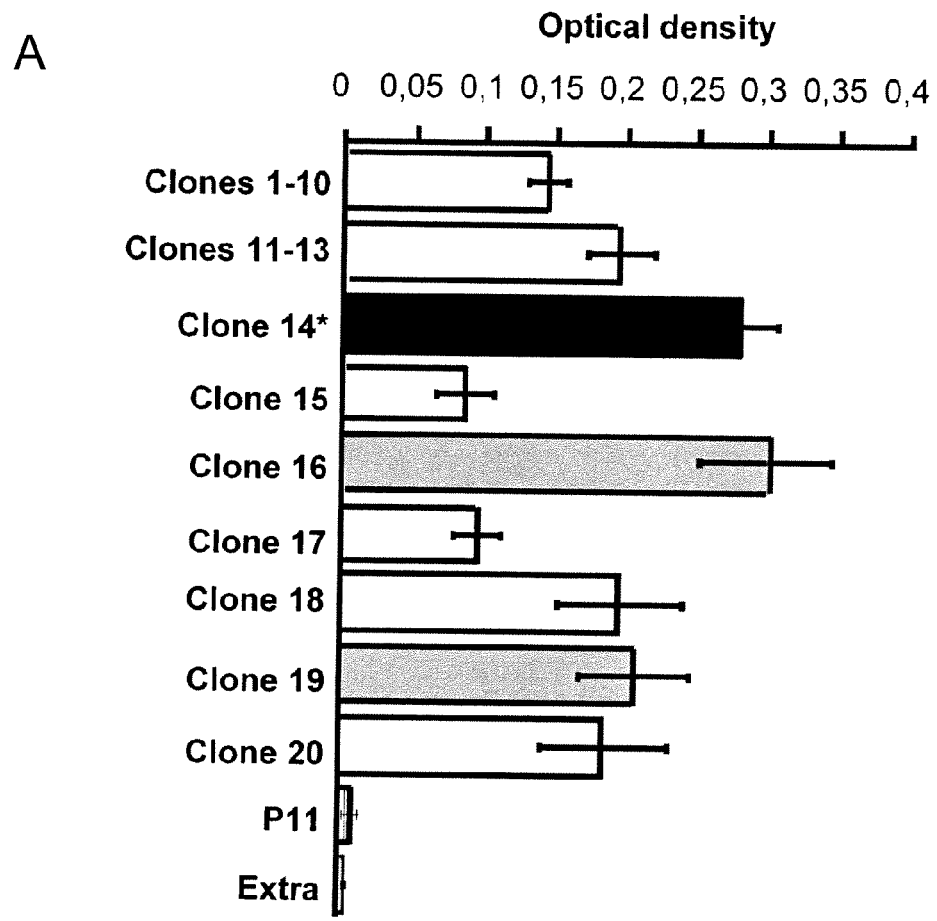
Figure 4:
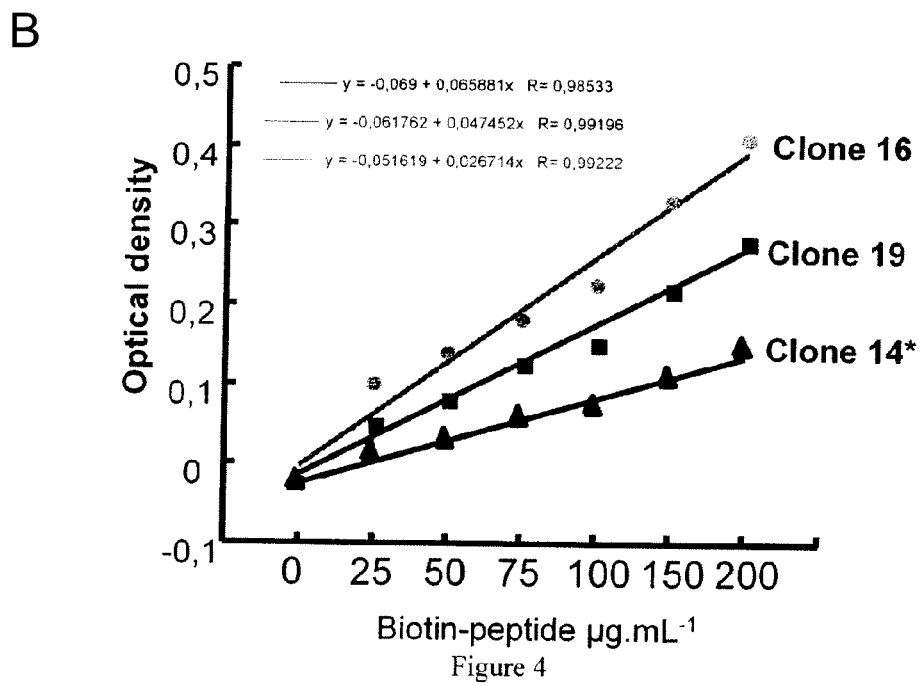
Figure 5:
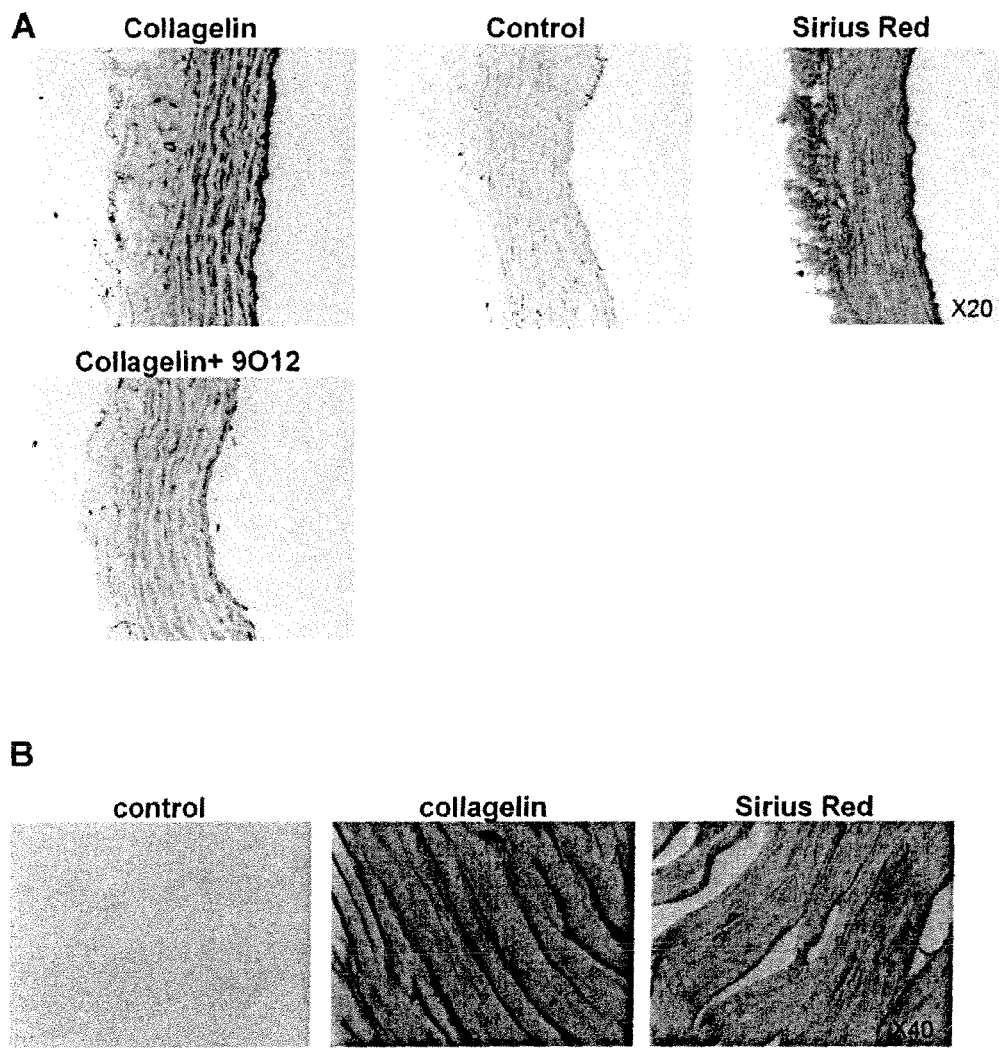

FIG. 4: Binding of the collagelin family peptides to collagen: A Peptides corresponding to the nine sequences identified from the 20 selected clones were synthesized coupled to biotin. 100 µg of each peptide was incubated with immobilized collagen and detected using peroxydase coupled streptavidine. Results are the mean±SD of three experiments made in triplicate. Pc corresponds to the cyclic non relevant peptide. * indicates collagelin. B Binding to collagen as a function of peptide concentration is shown for the three peptides. Increasing amounts of the synthetic peptides corresponding to the sequence of clones 16, 19 and 14 (collagelin) were incubated on collagen-coated plates and detected as above FIG. 5: Histochemical analysis of peptide binding to tissue collagen: A Frozen sections of the aorta from rats were incubated with biotin-collagelin or control peptide (300 µg/mL) which were detected using peroxydase coupled streptavidin. Sections were counter-colored with hematoxylin. Serial section were colored for collagen with Sirius red. In a competition experiment, the peptide was mixed with anti-GPVI IgGs 9O121.2 (300 µg/mL) before the addition to the aorta section. B Paraffin embedded sections of rat tail tendon were treated as above.

Figure 6:
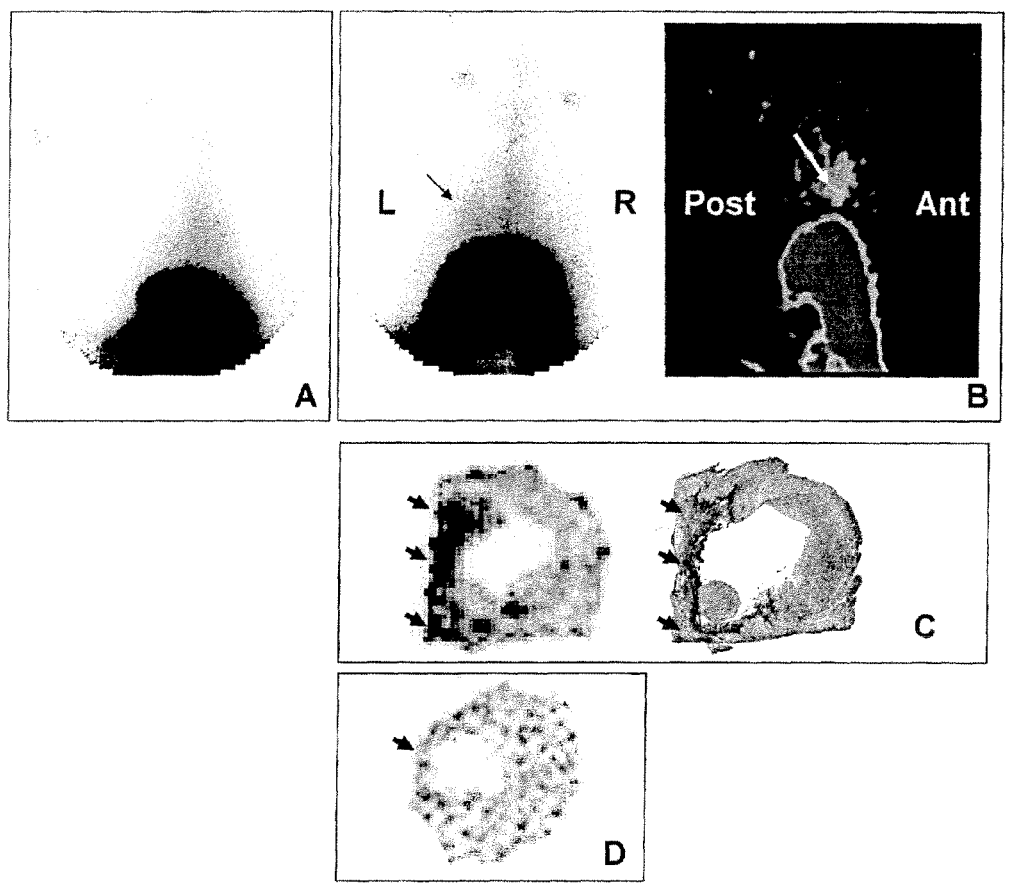

FIG. 6: In vivo scintigraphy, ex-vivo myocardial autoradiography and histology using collagelin-streptavidin-Tc99m. A: Planar thoracic scintigraphy of a control rat (sham). B: Planar and tomographic (sagittal view) thoracic images of a rat with fibrotic myocardial infarction: a hot spot (arrows) is seen in left ventricular myocardial area. C: Corresponding myocardial autoradiography and histology (Red Sirius coloration, specific for collagen), confirming tracer uptake in thinned fibrotic (red) myocardial scar (arrows). D: Control experiment: no activity is observed in myocardial scar of a rat injected with irrelevant Pc-streptavidin-Tc99m.

Figure 7:
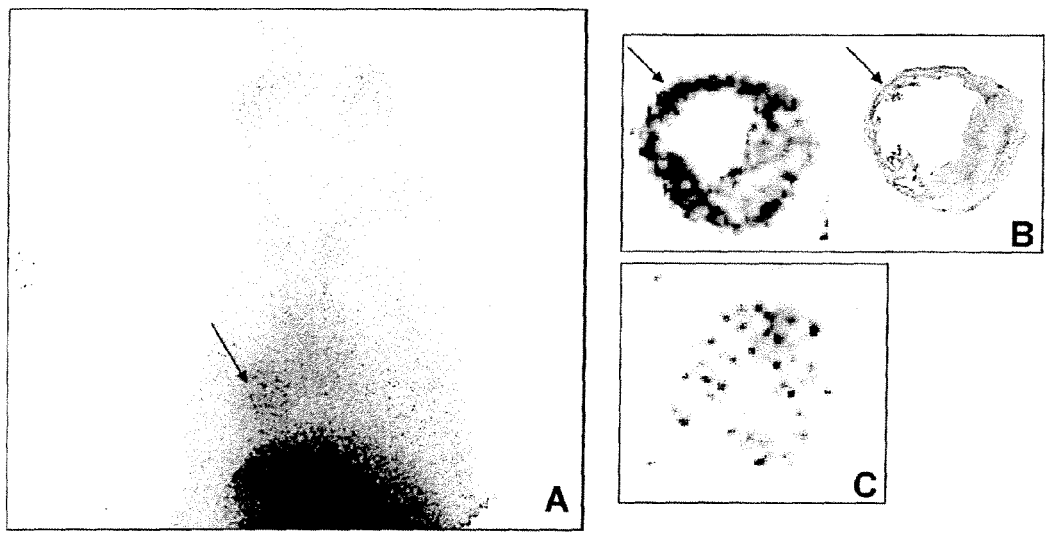

FIG. 7: In vivo scintigraphy, ex-vivo myocardial autoradiography and histology using collagelin-Tc99m: A: Planar thoracic scintigraphy of a rat with fibrotic myocardial infarction: a clear hot spot (arrows) is seen in left ventricular myocardial area. B: Corresponding myocardial autoradiography and histology (Red Sirius coloration, specific for collagen), confirming tracer uptake in thinned fibrotic (red) myocardial scar. C: Control experiment: very low activity is observed in myocardial infarction of a rat injected with irrelevant Pc-Tc99m.

Figure 8:
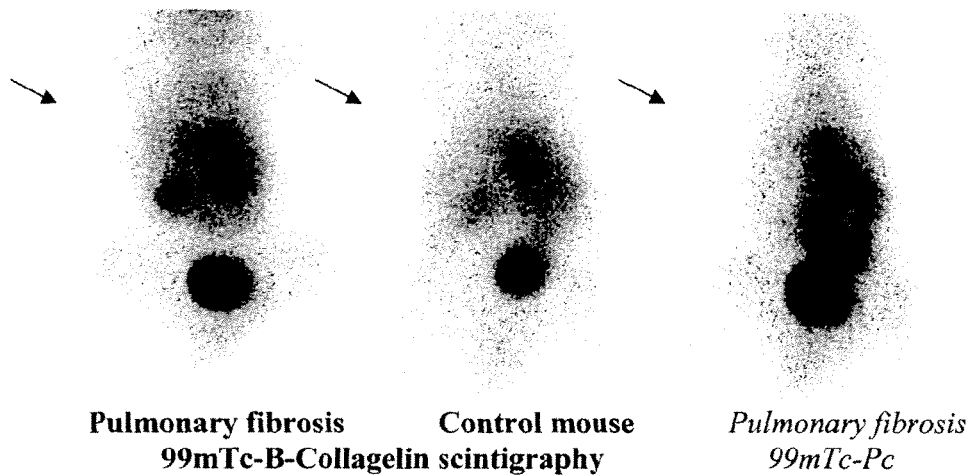
Figure 8:
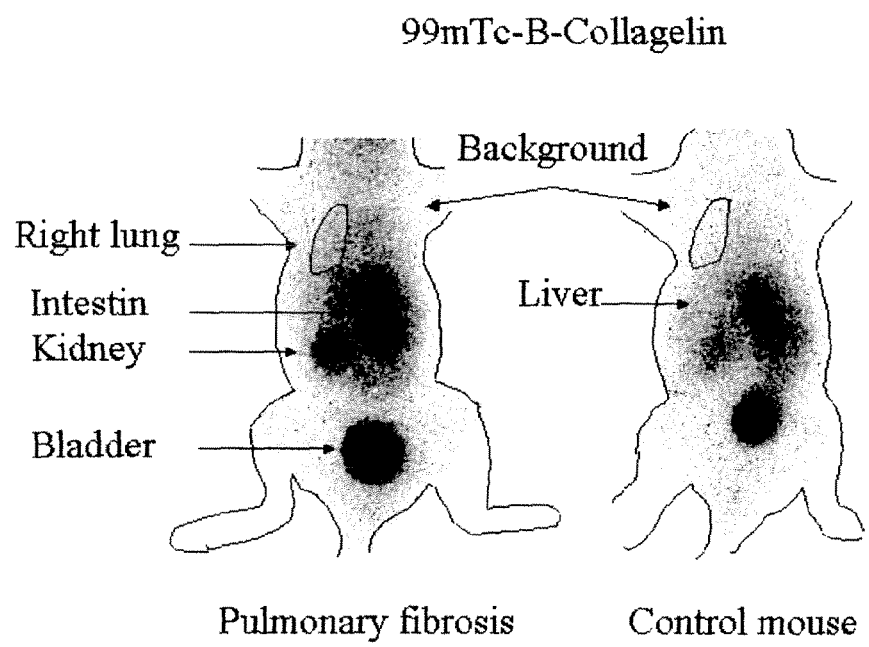

FIG. 8: In vivo pulmonary scintigraphy using 99m Tc-B-collagelin-

Figure 9:
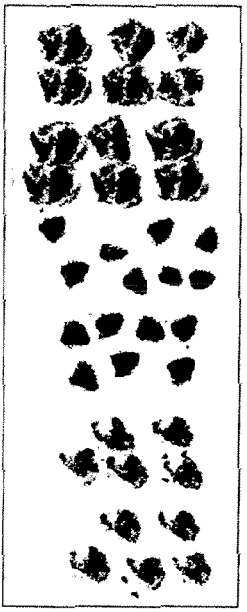
Figure 9:
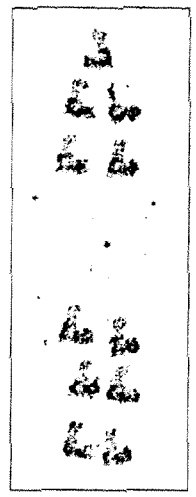
Figure 9:
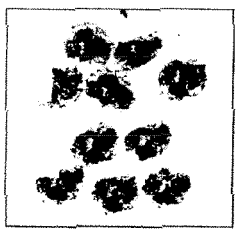
Figure 9:
Figure 9:
Figure 9:
Figure 9:

FIG. 9: Ex-vivo pulmonary autoradiography using 99m Tc-B-collagelin-. Sections (20 µM) of lungs from bleomycin-treated or control mice were exposed in an instant imager (Packard, USA) for autoradiography (sacrifice 3 h after 99m-Tc collagelin IV administration).

Figure 10:
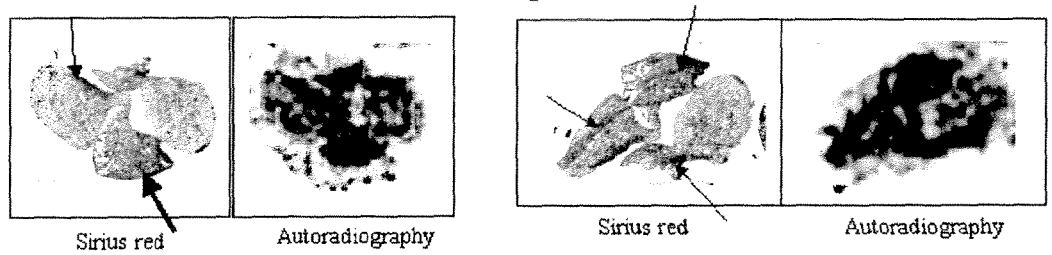
Figure 10:
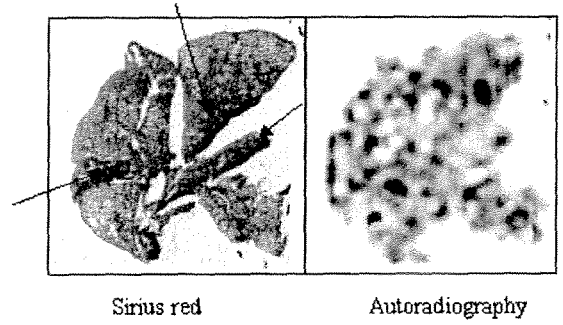

FIG. 10: Comparison of the uptake of 99m Tc-B-collagelin in lungs and the localisaton of fibrosis. Sections (20 µM) of lungs from bleomycin-treated mice were stained with sirius red after autoradiography. The fibrotic collagen enriched regions (arrows) superpose with 99m-Tc-collagelin uptake whereas no uptake of the control peptide is observed in fibrosis.

EXAMPLE 1

Identification and Characterization of a Peptidomimetic of Human Platelets Glycoprotein VI with Collagen Binding Activity. Its Use for Molecular Imaging of Fibrosis Material & Methods:
FliTrx™ Peptide Library and Anti-GPVI Antibody:
The FliTrx™ Random Peptide Display Library is an *E. coli*-based system allowing the screening of peptide interactions. The FliTrx™ Library was constructed in the pFliTrx™ vector (Lu Z. et al. 1995). A diverse library of random dodecapeptides ($10^8$) is positioned in the active site loop of the thioredoxin protein (trxA), inside the dispensable region of the bacterial flagellin gene (fliC). The resultant recombinant fusion protein (FLITRX) is exported and assembled into partially functional flagella on the bacterial cell surface. The dodecapeptides are displayed on the cell surface in a conformationally constrained by a disulfide bridge. The FliTrx™ random peptide library, based on the system was obtained from Invitrogen (San Diego, Calif.).

The anti-human platelet GPVI 9O12.2 IgGs and the soluble recombinant GPVI-Fc fusion protein were obtained as previously described (Lecut C. et al. 2003).

Screening of the Random Peptide Display Library:
Bacterial cultures and general panning methods were conducted according to the manufacturer's protocol. Briefly, the pFliTrx™ vector with the $P_L$ promoter from bacteriophage that drives expression was propagated in *E. coli* GI826 strain (F-, lacIq, ampC::$P_{trp}$ cI, ΔfliC, ΔmotB, eda::Tn10). Bacteria harboring the plasmid, were grown overnight at 25° C. in IMC medium [1% M9 salts (40 mM $Na_2HPO_4$, 20 mM $KH_2PO_4$, 8.5 mM NaCl, 20 mM $NH_4Cl$), 0.2% casamino acids, 0.5% glucose, 1 mM $MgCl_2$] containing 100 µg/mL ampicillin. Expression of the thioredoxin-flagellin fusion proteins containing the peptide inserts were induced by adding $10^8$ cells (3 mL) of the overnight culture to 50 mL IMC medium containing 100 µg/mL ampicillin and 100 µg/mL tryptophan.

The cultures were grown for 6 h at 25° C. After the 6 hours incubation, 10 mL of the induced E. coli culture were removed and mixed to 1% non-fat dry milk, NaCl (150 mM) and alpha-methyl mannoside 1% (final concentrations). The resulting solution was used as a peptide library ready for screening as follows.

Sterile tissue culture plates (Nunc) were coated overnight at 4° C. with 20 µg of the 9O12.2 IgG in 1 mL of sterile phosphate-buffered saline (PBS, pH7.4). Plates were washed with 10 mL sterile water and incubated with 10 ml of a blocking solution (150 mM NaCl, 1% w/v non-fat dry milk, 1% w/v alpha-methyl mannoside and 100 µg/mL ampicillin in IMC medium) under gentle agitation for 1 h. Aliquots (5 ml) of the induced bacterial culture were then added to the plates. The plates were then gently agitated at 50 rpm on a shaker for 1 min and incubated for 1 h at 25° C. The bacterial suspension was then discarded and plates were washed by gentle agitation for 5 min with 4 mL of IMC medium containing ampicillin and alpha-methyl mannoside. After four additional washings, bound bacteria were detached with 1 mL IMC by vigorous agitation for 30 s. Small aliquots of the bacterial suspension were diluted in IMC medium and spread evenly onto RMG (1% M9 salts, 2% casamino acids, 0.5% glucose, 1 mM $MgCl_2$, 100 µg/mL ampicillin and 1.5% agar) plates and then incubated overnight at 37° C. After each panning, bacteria were frozen at −80° C. After five rounds of biopanning, bacterial colonies were randomly picked from the RMG plates, amplified and induced for further identification.

Western Blotting Analysis:

Identification of positive clones by Western blotting was done essentially according to the manufacturer's protocol. Briefly, 10 mL of the amplified clone culture was transferred into 2 ml RM medium (1% M9 salts, 2% casamino acids, 1% glycerol, 1 mM MgCl2) containing 100 µg/ml ampicillin, and grown to saturation at 30° C. with shaking. A 40 µL sample from the overnight culture was inoculated at 37° C. in 2 mL IMC containing 100 µg/mL ampicillin and 100 µg/mL tryptophan until the cell density reaches $A_{600nm}$ 0.5-0.6. A 1.5 mL of induced cell culture was harvested by centrifugation at 10,000 g for 5 min. The pellet was resuspended in SDS-polyacrylamide gel-loading buffer, boiled for 5 min. Proteins were separated by electrophoresis in 12% polyacrylamide gel and blotted onto nitrocellulose by passive transfer overnight. Membranes were blocked with 2.5% Blotto/PBS for 2 h at room temperature, then incubated with 9O12 IgGs, 10 µg/mL in 1% BSA/PBS, for 2 h. After being washed three times with 0.1% Tween20/PBS, membranes were incubated with horseradish peroxydase (AP)-conjugated rabbit anti-mouse IgG for 1.5H at room temperature. After a further three washes procedure, bound IgGs were detected using NBT/BCIP.

DNA Sequencing:

Plasmid DNAs of the selected clones were isolated using standard protocols of plasmid DNA extraction (Sambrook and Russel, 2001). The nucleotide sequences were determined using a PRISM 310 automated DNA sequencer (Applied Biosystems, Foster city, CA) and the FliTrx™ forward sequencing primer (5'-ATT CAC CTG ACT GAC GAC-3') (SEQ ID NO: 31). The peptide sequence of each selected clone was deduced from DNA sequencing.

Peptide Synthesis:

One sequence amongst the ten identified was selected for large scale peptide synthesis and further characterization. The peptide was synthesized either free or biotinylated at the N-terminal end via a short flexible spacer (SGSG) (SEQ ID NO:32) sequence. Cyclisation was obtained by disulfide bridging of the cysteine residues (C5 and C22) flanking the sequence. The carboxyl function at the C-terminal end of the peptide was substituted by an amide. Peptides were prepared by the solid-phase method of Merrifield, with a semi-automatic multisynthetizer NPS 4000 (NeoMPS, Strasbourg, France). The sequence of the peptide so obtained was: SGS-GCGPRVMHGLHLGDDEGPC (SEQ ID NO: 22). The quality of synthesized peptides (biotinylated and non-biotinylated) was evaluated by HPLC and mass spectrometry. Said polypeptide was named collagelin.

The non cyclic biotinylated peptide (SGSGVNVYAVT-KENTIINPSENGD (SEQ ID NO:34)) and the cyclic peptide Pc (SGSGCGPNDANHDAVDNARGPC (SEQ ID NO:35)), biotinylated at the N-terminus (Mimotopes, Clayton Victoria, Australia) were used as irrelevant peptides for control experiments.

Binding Experiments:

Peptide binding to protein targets was analyzed using surface plasmon resonance and solid phase assays.

Surface Plasmon Resonance (SPR):

A Biacore 2000 instrument (GE Healthcare Europe GmbH, Orsay, France) (Université Paris 7, Institut Jacques Monod, Paris, France) was used to characterize the binding properties of the synthesized peptides. Biotinylated peptides (~20 RU) were covalently coupled to the surface of a SA-sensorchip.

The 9O12.2 IgG was injected over the immobilized peptide in HBS-EP buffer [0.01 M HEPES pH 7.4, 0.15 M NaCl, 0.005% polysorbate 20 (v/v)] at a flow rate of 20 µL·min-1 at 25° C. Glycine-HCl (10 mM pH 2.5) was injected for 30 s at 20 µL·min-1 to regenerate the sensorchip between each sample. Sensorgrams were analyzed with the BIA evaluation version 3.1 software. Kinetic constants (kon, koff) were deduced from the analysis of association and dissociation rates at four different IgG concentrations ranging from 1.25 to 10 µg·$mL^{-1}$. The dissociation constant KD was calculated from KD=koff/kon. Sensorgrams were analyzed with the BIAevaluation version 3.1 software. In some experiments, the peptide was reduced by DTT on the sensor chip before injection of the IgG. Competition experiments were performed by mixing the IgG with recombinant soluble GPVI (25 µg·$mL^{-1}$). Collagen binding to the peptide was analysed by injecting type I equine collagen (Collagen Horm, Nycomed. Germany) (200 µg·$mL^{-1}$ in EBS-EP buffer) onto the peptide-coated sensorchip.

In other experiments, fibrillar collagen was manually immobilized on a CM5-sensorchip according to the manufacturer's instructions (Biacore, Uppsala, Sweden). The biotinylated peptide (125; 250, 500 and 1000 µg/mL) was injected on immobilized collagen at 25° C. with a flow rate of 20 µL·min-1. In competition experiments, the peptide was pre-incubated with recombinant soluble human GPVI-Fc or the 9O12.2 IgGs before injection onto the surface. The surface plasmon resonance intensity was monitored and data analyzed using BioEval2.0 (Biacore).

Solid Phase Assays:

Proteins [type I equine fibrillar collagen (Horm), bovine fibrinogen (Sigma), human fibronectin (Sigma), rat vitronectin (Sigma), murine laminin (Gibco), and bovine serum albumin (BSA Sigma)] were coated (1 µg/well) on microtitration plates (Immulon 2 Dynex vWR) for 24 hours at 4° C. After saturation of free sites with BSA, biotinylated FLIGPVI (SEQ ID NO:33) peptide (50 µg/ml) was added to the wells for 2 hours. The peptide bound to the wells was then detected using extravidin-HRP and orthophenyldiamine as substrate.

Histochemical Analysis:

After freezing in 2-methyl butane, 8 µm sections of thoracic aorta from Lewis rats were cut on a cryostat microtome.

Inactivation of endogenous peroxydase, endogenous biotin sites and non specific sites were blocked by 0.3% H2O2 for 20 min, the biotin-blocking system (DAKO) and 1% BSA. After each step, the sections were washed with TBS pH7.6. Biotinylated peptides (200 μg/mL) were applied to the sections overnight at 4° C. After three washing steps, staining was performed using a peroxydase-labeled streptavidin (DAKO) and diaminobenzidine. Sections were counter-colored with hematoxylin-eosin (Merck).

Rat tail tendon was excised and embedded with tissue-Tek OCT at −20° C. Sections of 20 μM were cut and further processed as above.

Alternatively, frozen sections were fixed with formol for 10 min. After rehydratation, collagen was colored using Sirius Red.

Peptide Radiolabeling:

Labeling of Streptavidin with technetium-99m: Briefly streptavidin was dissolved in 0.01% acetic acid to a concentration of 1 mg·mL-1. For labeling, reactants were mixed for 1 min in the following order: first 10 μL of streptavidin followed by 4 μL of stannous (sn-PYP) and 2 μL of KBH4 (10 mg/ml in 0.1N NaOH), and 740 MBq of technetium-99m in 50-100 μL. Thirty min later, the solution was ready for injection. The quality control was performed with paper chromatography using methyl-cetone. The labeled streptavidin was unable to migrate. Free technetium migrated with the solvent front. High efficiency of labeling was obtained, superior to 96% at 30 min. Labeled streptavidin was mixed with biotin-collagelin in a molar ratio of one to four immediately before injection.

Collagelin SGSGCGPRVMHGLHLGDDEGPC (SEQ ID NO:22) was directly labeled using the same procedure, concentrations. (10 μL of 0.01% collagelin 1 mg·mL-1) and control as above. In any case high efficiency of labeling was obtained, superior to 96% at 30 min.

For control analyses, the cyclic Pc biotinylated peptide was used, after radiolabeling with 99 mTc-streptavidin or directly by Tc-99m, using the above described procedures.

The labeled streptavidin and of peptides was stable for at least three hours and then decreased with 40 to 50% free technetium at 6 hours. Labeled products were intravenously injected at the dose of 70 MBq/animal.

In Vivo Scintigraphic Imaging:

Male Wistar rats (Arland, France) were housed in a temperature- and humidity-controlled environment on a 12:12 h light-dark cycle, and were fed standard rat chow and water ad libitum. Myocardial infarction of the left ventricle was obtained by permanent ligature of the left descending coronary artery while the rats were under general anesthesia [1 ml/kg ip ketamine (Imalgène 500, Merial) and 0.5 ml/kg ip xylazine (2% Rompun, Bayer)] and positive pressure ventilation, as described (Fishbein M C. et al. 1978; Sarda-Mantel L. et al. 2006). This protocol is performed under the authorization of the French Direction des Services Vétérinaires (Authorization No. 75-214). Two types of control animals were used: healthy rats, and rats in which a simple throracotomy (sham-operated) was performed.

Radionucleide imaging was performed three to four weeks after the coronary ligature (or throracotomy) in order to the lesions to be healed. Labeled peptide was intravenously administrated to anesthetized animals (Pentobarbital 6 mg/100 g, BW, Ceva Santé Animale, France intraperitoneal injection) within 2 h of radiolabeling. Scintigraphic images were obtained 0-2 h, 4 h, 6 h, 10 h and 24 h after injection of 99 mTc-streptavidin-biotinylated peptide (74 MBq), 0-2 h and 4 h after injection of 99 mTc-biotinylated peptide (74 MBq), under pentobarbital anaesthesia (4 mg/100 g BW, Ceva Santé Animale, France). Planar and tomographic 1 h acquisitions were performed using a dedicated small animal yIMAGER-S/CT system (Biospace Mesures, Paris, France) equipped with 2 parallel low-energy high-resolution collimators (matrix 128×128, 15% energy window centered on 140 KeV). ANX uptake in left cardiac area was visually assessed. Also two regions of interest were drawn on the scintigrams, over the heart and over the right lung. Mean activity (cpm) per pixel was determined in each region of interest. Then heart to lung activity ratios (HLR) were calculated on planar images, as well as on transversal tomographic images.

Quantitative Autoradiography and Histology:

After sacrificing the animals, the heart was removed and frozen, then 20 micrometer thick myocardial sections were cut perpendicular to the short axis of the ventricles in a cryostat, then exposed in a radioimager (Instant Imager, Packard, Meriden, USA) during 12 h. According to calibration studies performed as previously reported, with activity standards of tissue-equivalent homogenates, 50 counts/mm2 of 99 mTc-annexinV approximated 210 kBq/mg in autoradiography (Petegnief Y. et al. 1998). Then the myocardial sections used for autoradiography as well as five micrometer contiguous heart sections fixed in acetone (−20° C.), were stained with hematoxylin-eosin and Sirius red to determine the location and extent of fibrotic myocardial scar.

Results:

Identification of 9O12.2-Binding Peptides:

After five rounds of biopanning of the combinatorial library of dodecamer constrained peptides using 9O12.2 IgGs, several individual bacterial clones were obtained. Twenty clones were selected and analyzed by immunoblotting using the IgG9O12.2. (FIG. 1A). These clones produced a fusion flagellar protein that was labelled by 9O12.2 indicating that it contained a peptide recognized by the antibody.

DNA sequencing of the 20 clones resulted in the identification of 9 peptide sequences shown on Table 1).

TABLE 1

Amino-acid alignment (Fasta format) of the 20 clones sequenced after screening of the FliTrx random peptide display library against immobilized 9012 IgG.

| Clone | Sequence |
| --- | --- |
| 1 | RFMHGLQLWADE (SEQ ID NO: 3) |
| 2 | RFMHGLQLWADE (SEQ ID NO: 3) |
| 3 | RFMHGLQLWADE (SEQ ID NO: 3) |
| 4 | RFMHGLQLWADE (SEQ ID NO: 3) |
| 5 | RFMHGLQLWADE (SEQ ID NO: 3) |
| 6 | RFMHGLQLWADE (SEQ ID NO: 3) |
| 7 | RFMHGLQLWADE (SEQ ID NO: 3) |
| 8 | RFMHGLQLWADE (SEQ ID NO: 3) |
| 9 | RFMHGLQLWADE (SEQ ID NO: 3) |
| 10 | RFMHGLQLWADE (SEQ ID NO: 3) |
| 11 | RVMHGLQLWADE (SEQ ID NO: 4) |
| 12 | RVMHGLQLWADE (SEQ ID NO: 4) |
| 13 | RVMHGLQLWADE (SEQ ID NO: 4) |
| 14 | RVMHGLHLGDDE (SEQ ID NO: 2) |

TABLE 1-continued

Amino-acid alignment (Fasta format) of the 20
clones sequenced after screening of the FliTrx
random peptide display library against immobilized
9012 IgG.

| Clone | Sequence |
|---|---|
| 15 | RVMHGLHLWDDE (SEQ ID NO: 5) |
| 16 | RVMHGLQLWDDE (SEQ ID NO: 6) |
| 17 | RVMHGLHLWADE (SEQ ID NO: 7) |
| 18 | FVMHGLHLGDDE (SEQ ID NO: 8) |
| 19 | PVMHGLHLWDDE (SEQ ID NO: 9) |
| 20 | RVMHGLLLGADE (SEQ ID NO: 10) |

Underlined is the sequence of the peptide that has been selected for synthesis.

These sequences differ from each other by one to four residues. None of these sequences was registered in databases.

The sequence of the clone 14 was selected for synthesis since the corresponding clone produced the more intense signal in immunoblotting with 9O12.2 (FIG. 1A). The following constrained peptide SGSGCGP RVMHGLHLGDDEGPC (SEQ ID NO:22). (designed as collagelin) was synthesized conjugated or not with biotin linked to the N-terminal end (designed "biotin-collagelin"). The purity of both peptides was higher than 95% as determined by HPLC analysis. Their molecular mass were 2155 and 2405 Da respectively.

The peptide was analyzed for its capacity to bind to 9O12.2 IgG, and to compete with GPVI in solid phase assays. Using surface plasmon resonance, 9O12.2 IgGs were found to bind to immobilized biotin-collagelin in a dose-dependent manner (FIG. 1B). The deduced KD was of $10^{-6}$ M. When biotin-collagelin was submitted to disulfide bridges reduction, it lost the capacity to bind 9O12.2 IgGs (FIG. 1C) in agreement with the previously reported observation that the 9O12.2 epitope is conformational (Lecut C. et al. 2003). Furthermore, 9O12.2 failed to bind to the peptide in the presence of recombinant soluble GPVI (GPVI-Fc) (FIG. 1D) indicating that GPVI and collagelin competed for the binding to 9O12.2.

Binding to Collagen:

These data led us to postulate that collagelin mimics at least in part the epitope of 9O12.2 on GPVI. As 9O12.2 neutralizes GPVI binding to collagen, we hypothesized that collagelin could at least in part mimic the collagen binding site of GPVI. We thus tested the capacity of collagelin to interact with collagen.

Using the streptavidin-coated sensorship onto which biotin-collagelin was immobilized we observed binding of type I collagen to the surface (FIG. 2A). Type I collagen was then immobilized onto a CM5 sensorchip through an amine-coupling procedure. Using increasing concentrations of biotin-collagelin (125; 250, 500 and 1000 µg/mL), we observed a dose dependent binding. Analysis of the sensorgrams allowed to calculate a KD of $1.10^{-7}$ M. (FIG. 2B).

Peptide interaction with collagen was further analyzed using collagen immobilized on microtitration plates. When compared to the irrelevant peptide, biotin-collagelin (50 µg/mL) significantly bound to collagen (FIG. 3A). Binding was completely inhibited in the presence of recombinant soluble GPVI or in the presence of 9O12.2 IgGs (FIG. 3A). In contrast, a second anti-GPVI monoclonal antibody, 3J24.2, that binds to a different epitope than 9O12.2 and does not neutralize GPVI interaction with collagen (Lagrue-Lak-Hal A H. et al. 2001), did not inhibit the binding of biotin-collagelin to collagen. Altogether, these results demonstrate that collagelin and GPVI bind to the same or overlapping sites at the surface of collagen. Due to its collagen binding properties the peptide was named collagelin.

In order to precise the specificity of collagelin, we have tested its capacity to bind to different immobilized macromolecules from the extracellular matrix: fibronectin, vitronectin and mouse laminin or accumulated at sites of vascular lesions (fibrinogen/fibrin) (FIG. 3B). Collagelin did not bind to fibrinogen, vitronectin and fibronectin significantly more than to bovine serum albumin. In contrast, it bound to laminin previously identified as a GPVI accessory ligand (Inoue O. et al. 2006). This result indicates that the sites of GPVI that interact with laminin and collagen share a common structure that is mimicked by collagelin. Furthermore, laminin was found to bind to collagelin by SPR analysis with a calculated KD of $1.83 \times 10^{-5}$ M. In contrast, a non relevant peptide did not bind to any of these proteins.

Eight synthetic peptides corresponding to the sequences of the other clones identified with 9O12.2 were synthesized and tested for their capacity to bind to collagen. All were found to bind to collagen when compared to the control non relevant peptides (FIG. 4) with variable efficiency.

Ex Vivo Labeling of Collagen with Collagelin:

Since GPVI binds to collagen at the sites of vascular damages we investigated whether collagelin was able to interact with vascular collagen by histochemistry analysis.

Frozen sections of paraffin embedded sections of rat aortas were incubated with the biotinylated collagelin I or irrelevant peptide. Bound peptides were detected using peroxydase coupled extravidine (FIG. 5A). A brown color developed on aorta sections with collagelin but not with the irrelevant peptide. The labeling was clearer on frozen sections of rat aortas (FIG. 7B) than on fixed sections. Labeling with collagelin coincided with the coloration of collagen with Sirius Red. In the presence of the anti-GPVI IgG 9O12.2 the intensity of the labeling with collagelin decreased indicating the specificity of the interaction between the peptide and the vascular matrix.

The capacity of collagelin to interact with non vascular collagen was next tested using sections of rat tail that contain high amounts of type I collagen (FIG. 5B). An intense labeling of fibers colored with Sirius red was observe with collagelin but not with the control peptide.

In Vivo Isotopic Molecular Imaging of Fibrosis:

Since collagelin heavily labeled collagen on histochemistry analysis, we hypothesized that it could be retained in vivo at sites of collagen accumulation. Collagelin was thus labeled and intravenously injected in rats presenting a healed myocardial infarct.

First, 8 rats (4 with myocardial infarction, 4 sham-operated) received mixed Tc-99m labeled streptavidin-biotinylated collagelin. The radiotracer showed high non specific liver uptake, and slow blood clearance (high blood pool activity was seen until 12 h post-injection). Visually, planar and tomographic images demonstrated significant tracer uptake in cardiac area in all rats with myocardial infarction at 4 h-6 h post injection (FIG. 6B), whereas no tracer uptake was observed in cardiac area of all sham-operated rats. Heart-to-lung ratio on planar scintigraphic images was 2.76+/−0.36 in rats with myocardial infarction versus 1.95+/−0.28 in sham-operated rats (p=0.003). On the frozen sections of the heart obtained 6 hours after the injection, the signal was accentuated in the infarct area in rats treated with the collagelin/Tc- 99m streptavidin mixture, with infarct-to-remote myocardium ratio of 2.00+/−0.70 (FIG. 6C). The infarct zone was enriched in collagen indicated by histology with Sirius red. Control experiments were performed in 6 rats with myocardial scar using a non specific 99 mTc-streptavidin-biotin-peptide: autoradiographic data obtained 6 h after injection revealed no or mild non specific tracer uptake in the infarcts with lower infarct-to-remote myocardium ratio than that obtained with collagelin (1.82+/−0.32 versus 2.61+/−0.19, p<0.01) (FIG. 6D).

Second, 12 rats (8 with myocardial infarction, 4 sham-operated) were injected with 99 mTc-collagelin. The radiotracer demonstrated early (<5 min) biliary excretion and fast blood clearance. Visually, significant tracer uptake was clearly seen on planar and tomographic images in cardiac area of 5/8 rats with myocardial infarction 1 h after tracer injection (FIG. 7A). Imaging was doubtful in the cardiac area of 2 other rats with myocardial infarction, and negative in 1. Increased tracer uptake was also observed in cutaneous scar and/or subcutaneous thoracic scar of 6/10 operated rats (4 with myocardial infarction, 2 sham-operated). Heart-to-lung ratio on planar scintigraphic images was 2.08+/−0.17 in rats with myocardial infarction versus 1.45+/−0.03 in sham-operated rats (p=0.03). On the frozen sections of the heart obtained 6 hours after the injection, the signal was accentuated in the infarct area in rats treated with infarct-to-remote myocardium ratio of 3.06+/−0.45 (FIG. 7B). The infarct zone was enriched in collagen indicated by histology with Sirius red. Control experiments were performed using a non specific 99 mTc-peptide: autoradiographic data obtained 4 h after injection revealed very low absolute tracer uptake in myocardial tissues (10% of that observed with 99 mTc-collagelin), and mild increased tracer uptake in infarcts compared to normal myocardium, corresponding to mild non specific tracer accumulation (infarct-to-remote-myocardium: 1.7) (FIG. 7C).

EXAMPLE 2

Imaging of Pulmonary Fibrosis by Scintigraphy Using $^{99}$Mtc-Labeled Collagelin Methods:

Male C57BL/6J mice, aged 6-7 weeks were kept in accordance with INSERM rules. On day 0, mice were administered 80 μg of bleomycin hydrochloride (Bleomycine Bellon, Aventis, France) intratracheally. Mortality was assessed daily over a 14 day period. Naïve mice were used as controls.

At day 14 mice received one intravenous injection of 99 mTc-B-collagelin or of 99 mTc-B-Pc (3 MBq). Then planar whole-body scintigraphic imaging (60 min duration) was performed 1 h after tracer injection, using Biospace Lab dedicated small animal gamma camera.

At the end of the experiment, animals were sacrificed and lung were dissected for gamma counting, autoradiography, and histology (Sirius red coloration).

Results:

Scintigraphy:

Significant 99 mTc-B-collagelin uptake was observed in pulmonary areas of the mice that received bleomycin (lung/muscle background activity ratio: 3.65±0.34), which was higher than that observed in pulmonary areas of control mice (lung/muscle background activity ratio: 1.56±0.01, p<0.02), and higher than 99 mTc-B-Pc uptake in pulmonary areas of bleomycin mice (lung/muscle background activity ratio: 2.20±0.11, p<0.03) (FIG. 8).

Autoradiography:

Autoradiographic studies confirmed higher 99 mTc-B-collagelin uptake on sections of the lung of mice with pulmonary fibrosis as compared to controls (mean counts/mm$^2$: 140±32 versus 61±10, NS), with heterogeneous distribution matched with that of Sirius red coloration. This result is highly suggestive of specific 99 mTc-B-collagelin uptake into fibrosis (FIG. 9).

The uptake of the control peptide in fibrotic lungs was significantly lower than that of 99 mTc-B-collagelin as indicated by an activity of 65±10 counts/per mm$^2$. Moreover control peptide uptake was not correlated with red Sirius coloration (FIG. 10).

Conclusion:

99 mTc-labeled collagelin permit an efficient and specific imaging of pulmonary fibrosis in mice.

REFERENCES

Algin et al 1994, Tetrahedron Lett. 35:9633-9636

Clemetson J M, Polgar J, Magnenat E, Wells T N, Clemetson K J. The platelet collagen receptor glycoprotein VI is a member of the immunoglobulin superfamily closely related to FcalphaR and the natural killer receptors. J Biol Chem. 1999; 274:29019-29024.

Cosemans J M, Kuijpers M J, Lecut C, Loubele S T, Heeneman S, Jandrot-Perrus M, Heemskerk J W. Contribution of platelet glycoprotein VI to the thrombogenic effect of collagens in fibrous atherosclerotic lesions. Atherosclerosis. 2005; 181:19-27

Davies J S The cyclisation of peptides and depsipeptides J Pept Sci 2003, 8:471-501

Davies J S. The cyclization of peptides and depsipeptides. J Pept Sci. 2003 August; 9(8):471-501. Review.

de Lédinghen V, Le Bail B, Rebouissoux L, Fournier C, Foucher J, Miette V, Castéra L, Sandrin L, Merrouche W, Lavrand F, Lamireau T. Liver Stiffness Measurement in Children Using FibroScan: Feasibility Study and Comparison With Fibrotest, Aspartate Transaminase to Platelets Ratio Index, and Liver Biopsy. J Pediatr Gastroenterol Nutr. 2007 October; 45(4):443-450.

Dumont B, Minullina I, Loyau S, Monteiro R C, Lacapere J J, Arocas V, Jandrot-Perrus M. Chimeric Fc Receptors Identify Ligand Binding Regions in Human Glycoprotein VI. J Mol Biol. 2006; 361:877-887

Fishbein M C, Maclean D, Maroko P R. Experimental myocardial infarction in the rat: qualitative and quantitative changes during pathologic evolution. Am J Pathol. 1978; 90:57-70

Fuster V. Role of platelets in the development of atherosclerotic disease and possible interference with platelet inhibitor drugs. Scand J Haematol Suppl. 1981; 38:1-38

Gawaz M, Konrad I, Hauser A I, Sauer S, Li Z, Wester H J, Bengel F M, Schwaiger M, Schomig A, Massberg S, Haubner R. Non-invasive imaging of glycoprotein VI binding to injured arterial lesions. Thromb Haemost. 2005; 93:910-913

Gawaz M, Konrad I, Hauser A I, Sauer S, Li Z, Wester H J, Bengel F M, Schwaiger M, Schömig A, Massberg S, Haubner R. Non-invasive imaging of glycoprotein VI binding to injured arterial lesions. Thromb Haemost. 2005 May; 93(5):910-3.

Horii K, Kahn M L, Herr A B. Structural basis for platelet collagen responses by the immune-type receptor glycoprotein VI. Blood. 2006; 108:936-942

Hruby et al 1994, Reactive Polymers 22:231-241

Inoue O, Suzuki-Inoue K, McCarty O J, Moroi M, Ruggeri Z M, Kunicki T J, Ozaki Y, Watson S P. Laminin stimulates spreading of platelets through integrin alpha6beta1-dependent activation of GPVI. Blood. 2006; 107:1405-1412

Jandrot-Perrus M, Busfield S, Lagrue A H, Xiong X, Debili N, Chickering T, Le Couedic J P, Goodearl A, Dussault B, Fraser C, Vainchenker W, Villeval J L. Cloning, characterization, and functional studies of human and mouse glycoprotein VI: a platelet-specific collagen receptor from the immunoglobulin superfamily. Blood. 2000; 96:1798-1807.

Kates et al 1993, Tetrahedron Lett. 34:1549-1552

Kehrel B, Wierwille S, Clemetson K J, Anders O, Steiner M, Knight C G, Farndale R W, Okuma M, Barnes M J. Glycoprotein VI is a major collagen receptor for platelet activation: it recognizes the platelet-activating quaternary structure of collagen, whereas CD36, glycoprotein IIb/IIIa, and von Willebrand factor do not. Blood. 1998; 91:491-499.

Kempton C L, Harvey R D, 3rd, Roberts H R. Novel therapeutic agents in the management of hemorrhage and thrombosis. Cardiovasc Hematol Agents Med Chem. 2006; 4:319-334

Kleinschnitz C, Pozgajova M, Pham M, Bendszus M, Nieswandt B, Stoll G. Targeting platelets in acute experimental stroke: impact of glycoprotein Ib, VI, and IIb/IIIa blockade on infarct size, functional outcome, and intracranial bleeding. Circulation. 2007; 115:2323-2330

Konishi H, Katoh Y, Takaya N, Kashiwakura Y, Itoh S, Ra C, Daida H. Platelets activated by collagen through immunoreceptor tyrosine-based activation motif play pivotal role in initiation and generation of neointimal hyperplasia after vascular injury. Circulation. 2002; 105:912-916.

Kunicki T J, Cheli Y, Moroi M, Furihata K. The influence of N-linked glycosylation on the function of platelet glycoprotein VI. Blood. 2005

Lagrue-Lak-Hal A H, Debili N, Kingbury G, Lecut C, Le Couedic J P, Villeval J L, Jandrot-Perrus M, Vainchenker W. Expression and function of the collagen receptor GPVI during megakaryocyte maturation. J Biol Chem. 2001; 276:15316-15325.

Lecut C, Arocas V, Ulrichts H, Elbaz A, Villeval J L, Lacapere J J, Deckmyn H, Jandrot-Perrus M. Identification of residues within human glycoprotein VI involved in the binding to collagen: evidence for the existence of distinct binding sites. J Biol Chem. 2004; 279:52293-52299

Lecut C, Feeney L A, Kingsbury G, Hopkins J, Lanza F, Gachet C, Villeval J L, Jandrot-Perrus M. Human platelet glycoprotein VI function is antagonized by monoclonal antibody-derived Fab fragments. J Thromb Haemost. 2003; 1:2653-2662

Lecut C, Schoolmeester A, Kuijpers M J, Broers J L, van Zandvoort M A, Vanhoorelbeke K, Deckmyn H, Jandrot-Perrus M, Heemskerk J W. Principal role of glycoprotein VI in alpha2beta1 and alphaIIbbeta3 activation during collagen-induced thrombus formation. Arterioscler Thromb Vasc Biol. 2004; 24:1727-1733

Li and Roller P P Cyclisation strategies in peptide derived drug design. Curr. Tp Med. Chem. 2002, 3:325-41.

Li P, Roller P P. Cyclization strategies in peptide derived drug design. Curr Top Med Chem. 2002 March; 2(3):325-41. Review.

Lu Z, Murray K S, Van Cleave V, LaVallie E R, Stahl M L, McCoy J M. Expression of thioredoxin random peptide libraries on the *Escherichia coli* cell surface as functional fusions to flagellin: a system designed for exploring protein-protein interactions. Biotechnology (NY). 1995; 13:366-372

Marlowe C K. Peptide cyclization on TFA labile resin using the trimethylsilyl (TMSE) ester as an orthogonal protecting group. Bioorganic & Medicinal Chemistry Letters, Volume 3, Issue 3, March 1993, Pages 437-440

Massberg S, Gawaz M, Gruner S, Schulte V, Konrad I, Zohlnhofer D, Heinzmann U, Nieswandt B. A crucial role of glycoprotein VI for platelet recruitment to the injured arterial wall in vivo. J Exp Med. 2003; 197:41-49.

McMurray et al 1994, Peptide Res. 7:195-206

Miura Y, Ohnuma M, Jung S M, Moroi M. Cloning and expression of the platelet-specific collagen receptor glycoprotein VI. Thromb Res. 2000; 98:301-309.

Morton L F, Hargreaves P G, Farndale R W, Young R D, Barnes M J. Integrin alpha 2 beta 1-independent activation of platelets by simple collagen-like peptides: collagen tertiary (triple-helical) and quaternary (polymeric) structures are sufficient alone for alpha 2 beta 1-independent platelet reactivity. Biochem J. 1995; 306:337-344.

Murray C J, Lopez A D. Alternative projections of mortality and disability by cause 1990-2020: Global Burden of Disease Study. Lancet. 1997 May 24; 349(9064):1498-504.

Mustard J F. Hemostasis and thrombosis. Semin Hematol. 1968; 5:91-106

Nakamura T, Jamieson G A, Okuma M, Kambayashi J, Tandon N N. Platelet adhesion to native type I collagen fibrils. Role of GPVI in divalent cation-dependent and -independent adhesion and thromboxane A2 generation. J Biol Chem. 1998; 273:4338-4344.

Nieswandt B, Aktas B, Moers A, Sachs U J. Platelets in atherothrombosis: lessons from mouse models. J Thromb Haemost. 2005; 3:1725-1736

Nieswandt B, Watson S P. Platelet-collagen interaction: is GPVI the central receptor? Blood. 2003; 102:449-461

Pallin and Tam 1995, J. Chem. Soc. Chem. Comm. 2021-2022

Penz S, Reininger A J, Brandl R, Goyal P, Rabie T, Bernlochner I, Rother E, Goetz C, Engelmann B, Smethurst P A, Ouwehand W H, Farndale R, Nieswandt B, Siess W. Human atheromatous plaques stimulate thrombus formation by activating platelet glycoprotein VI. Faseb J. 2005; 19:898-909

Petegnief Y, Petiet A, Peker M C, Bonnin F, Meulemans A, Le Guludec D. Quantitative autoradiography using a radioimager based on a multiwire proportional chamber. Phys Med Biol. 1998; 43:3629-3638

Sarda-Mantel L, Michel J B, Rouzet F, Martet G, Louedec L, Vanderheyden J L, Hervatin F, Raguin O, Vrigneaud J M, Khaw B A, Le Guludec D. (99m)Tc-annexin V and (111) In-antimyosin antibody uptake in experimental myocardial infarction in rats. Eur J Nucl Med Mol Imaging. 2006; 33:239-245

Schmidt and Langer 1997, J. Peptide Res. 49:67-73

Smethurst P A, Joutsi-Korhonen L, O'Connor M N, Wilson E, Jennings N S, Garner S F, Zhang Y, Knight C G, Dafform T R, Buckle A, MJ I J, De Groot P G, Watkins N A, Farndale R W, Ouwehand W H. Identification of the primary collagen-binding surface on human glycoprotein VI by site-directed mutagenesis and by a blocking phage antibody. Blood. 2004; 103:903-911

Takaya N, Katoh Y, Iwabuchi K, Hayashi I, Konishi H, Itoh S, Okumura K, Ra C, Nagaoka I, Daida H. Platelets activated by collagen through the immunoreceptor tyrosine-based activation motif in the Fc receptor gamma-chain play a pivotal role in the development of myocardial ischemia-reperfusion injury. J Mol Cell Cardiol. 2005

Talwalkar J A, Kurtz D M, Schoenleber S J, West C P, Montori V M. Ultrasound-based transient elastography for the detection of hepatic fibrosis: systematic review and meta-analysis. Clin Gastroenterol Hepatol. 2007 October; 5(10): 1214-20.

Taouli B, Tolia A J, Losada M, Babb J S, Chan E S, Bannan M A, Tobias H. Diffusion-weighted MRI for quantification of liver fibrosis: preliminary experience. AJR Am J Roentgenol. 2007 October; 189(4):799-806.

Tumelty et al 1994, J. Chem. Soc. Chem. Comm. 1067-1068

Vanhoorelbeke K, Ulrichts H, Schoolmeester A, Deckmyn H. Inhibition of platelet adhesion to collagen as a new target for antithrombotic drugs. Curr Drug Targets Cardiovasc Haematol Disord. 2003; 3:125-140.

Weidemann F, Niemann M, Herrmann S, Kung M, Stork S, Waller C, Beer M, Breunig F, Wanner C, Voelker W, Ertl G, Bijnens B, Strotmann J M. A new echocardiographic approach for the detection of non-ischaemic fibrosis in hypertrophic myocardium. Eur Heart J. 2007 Nov. 1; [Epub ahead of print]

The invention claimed is:

1. A polypeptide comprising an amino acid sequence consisting of:

X1-X2-MHGL-X7-L-X9-X10-DE    (SEQ ID NO: 1)

wherein
amino acid X1 is R, F or P;
amino acid X2 is F or V;
amino acid X7 is Q, H or L;
amino acid X9 is W or G and
amino acid X10 is A or D.

2. The polypeptide according to claim 1 comprising an amino acid sequence selected in the group consisting of RVMHGLHLGDDE (SEQ ID NO:2); RFMHGLQLWADE (SEQ ID NO:3); RVMHGLQLWADE (SEQ ID NO:4); RVMHGLHLWDDE (SEQ ID NO:5); RVMHGLQLWDDE (SEQ ID NO:6); RVMHGLHLWADE (SEQ ID NO:7); FVMHGLHLGDDE (SEQ ID NO:8); PVMHGLHLWDDE (SEQ ID NO:9); and RVMHGLLLGADE (SEQ ID NO:10).

3. The polypeptide according to claim 2 comprising an amino acid sequence as set forth in SEQ ID NO:2.

4. The polypeptide according to claim 1 comprising an amino acid sequence consisting of:

CGP-X1-X2-MHGL-X7-L-X9-X10-DEGPC    (SEQ ID NO: 11)

wherein
amino acid X1 is R, F or P;
amino acid X2 is F or V;
amino acid X7 is Q, H or L;
amino acid X9 is W or G and
amino acid X10 is A or D.

5. The polypeptide according to claim 4 comprising an amino acid sequence consisting of:

SGSGCGP-X1-X2-MHGL-X7-L-X9-X10-DEGPC    (SEQ ID NO: 21)

wherein
amino acid X1 is R, F or P;
amino acid X2 is F or V;
amino acid X7 is Q, H or L;
amino acid X9 is W or G and
amino acid X10 is A or D.

6. The polypeptide according to claim 1, wherein said polypeptide is labelled with a detectable substance.

7. A cyclic polypeptide wherein the polypeptide according to claim 4 is cyclised via a disulfide bond between the two cysteine residues.

8. The cyclic polypeptide according to claim 7 comprising the formula of:

(SEQ ID NO: 11)

$$\text{CGP-X1-X2-MHGL-X7-L-X9-X10-DEGPC}$$
$$\;\;\;\;|\;\;\;\;\;\;\;\;\;\;\;\;\;\;\;\;\;\;\;\;\;\;\;\;\;\;\;\;\;\;\;\;\;\;\;\;\;|$$
$$S_1\text{―――――――――――――}S_1,$$

wherein $S_1$ is sulfur.

9. The cyclic polypeptide according claim 7, wherein said polypeptide is labelled with a detectable substance.

10. The cyclic polypeptide according to claim 9 comprising the formula of:

(SEQ ID NO: 21)

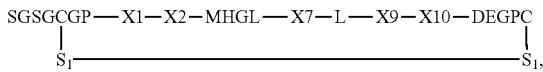

wherein $S_1$ is sulfur.

11. A cyclic polypeptide comprising the formula of:

(SEQ ID NO: 11)

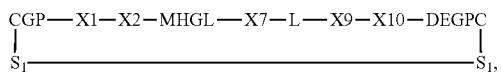

wherein $S_1$ is sulfur; amino acid X1 is R, F, or P; amino acid X2 is F or V; amino acid X7 is Q, H or L; amino acid X9 is W or G and amino acid X10 is A or D.

12. An isolated nucleic acid molecule encoding a polypeptide according to claim 1.

13. A vector comprising a nucleic acid according to claim 12.

14. A host cell, which has been transformed by a nucleic acid according to claim 12.

15. An imaging agent comprising the labelled polypeptide according to claim 6.

16. A pharmaceutical composition comprising an imaging agent according to claim 15.

17. A labelled cyclic polypeptide comprising the formula of:

(SEQ ID NO: 11)

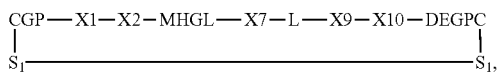

wherein $S_1$ is sulfur; amino acid X1 is R, F, or P; amino acid X2 is F or V; amino acid X7 is Q, H or L; amino acid X9 is W or G and amino acid X10 is A or D and wherein the polypeptide is labelled with a detectable substance.

18. A method for imaging of a condition associated with fibrosis comprising the administration of the imaging agent according to claim 15 to a subject in need thereof.

19. The method according to claim 18 wherein said condition associated with fibrosis is selected from the group consisting of lung fibrosis, liver kidney fibrosis, heart fibrosis, vascular system fibrosis, skin fibrosis, eye fibrosis, bone and bone marrow fibrosis.

20. An imaging agent comprising the labelled cyclic polypeptide according to claim 9.

* * * * *

```
                           SEQUENCE LISTING

<160> NUMBER OF SEQ ID NOS: 35

<210> SEQ ID NO 1
<211> LENGTH: 12
<212> TYPE: PRT
<213> ORGANISM: artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: X is R, F or P
<220> FEATURE:
<221> NAME/KEY: MISC_FEATURE
<222> LOCATION: (2)..(2)
<223> OTHER INFORMATION: X is F or V
<220> FEATURE:
<221> NAME/KEY: MISC_FEATURE
<222> LOCATION: (7)..(7)
<223> OTHER INFORMATION: X is Q, H or L
<220> FEATURE:
<221> NAME/KEY: MISC_FEATURE
<222> LOCATION: (9)..(9)
<223> OTHER INFORMATION: X is W or G
<220> FEATURE:
<221> NAME/KEY: MISC_FEATURE
<222> LOCATION: (10)..(10)
<223> OTHER INFORMATION: X is A or D

<400> SEQUENCE: 1

Xaa Xaa Met His Gly Leu Xaa Leu Xaa Xaa Asp Glu
1               5                  10

<210> SEQ ID NO 2
<211> LENGTH: 12
<212> TYPE: PRT
<213> ORGANISM: artificial
<220> FEATURE:
<223> OTHER INFORMATION: synthetic

<400> SEQUENCE: 2

Arg Val Met His Gly Leu His Leu Gly Asp Asp Glu
1               5                  10

<210> SEQ ID NO 3
<211> LENGTH: 12
<212> TYPE: PRT
<213> ORGANISM: artificial
<220> FEATURE:
<223> OTHER INFORMATION: synthetic

<400> SEQUENCE: 3

Arg Phe Met His Gly Leu Gln Leu Trp Ala Asp Glu
1               5                  10

<210> SEQ ID NO 4
```

```
<211> LENGTH: 12
<212> TYPE: PRT
<213> ORGANISM: artificial
<220> FEATURE:
<223> OTHER INFORMATION: synthetic

<400> SEQUENCE: 4

Arg Val Met His Gly Leu Gln Leu Trp Ala Asp Glu
 1               5                  10

<210> SEQ ID NO 5
<211> LENGTH: 12
<212> TYPE: PRT
<213> ORGANISM: artificial
<220> FEATURE:
<223> OTHER INFORMATION: synthetic

<400> SEQUENCE: 5

Arg Val Met His Gly Leu His Leu Trp Asp Asp Glu
 1               5                  10

<210> SEQ ID NO 6
<211> LENGTH: 12
<212> TYPE: PRT
<213> ORGANISM: artificial
<220> FEATURE:
<223> OTHER INFORMATION: synthetic

<400> SEQUENCE: 6

Arg Val Met His Gly Leu Gln Leu Trp Asp Asp Glu
 1               5                  10

<210> SEQ ID NO 7
<211> LENGTH: 12
<212> TYPE: PRT
<213> ORGANISM: artificial
<220> FEATURE:
<223> OTHER INFORMATION: synthetic

<400> SEQUENCE: 7

Arg Val Met His Gly Leu His Leu Trp Ala Asp Glu
 1               5                  10

<210> SEQ ID NO 8
<211> LENGTH: 12
<212> TYPE: PRT
<213> ORGANISM: artificial
<220> FEATURE:
<223> OTHER INFORMATION: synthetic

<400> SEQUENCE: 8

Phe Val Met His Gly Leu His Leu Gly Asp Asp Glu
 1               5                  10

<210> SEQ ID NO 9
<211> LENGTH: 12
<212> TYPE: PRT
<213> ORGANISM: artificial
<220> FEATURE:
<223> OTHER INFORMATION: synthetic

<400> SEQUENCE: 9

Pro Val Met His Gly Leu His Leu Trp Asp Asp Glu
 1               5                  10

<210> SEQ ID NO 10
<211> LENGTH: 12
<212> TYPE: PRT
```

```
<213> ORGANISM: artificial
<220> FEATURE:
<223> OTHER INFORMATION: synthetic

<400> SEQUENCE: 10

Arg Val Met His Gly Leu Leu Leu Gly Ala Asp Glu
1               5                   10

<210> SEQ ID NO 11
<211> LENGTH: 18
<212> TYPE: PRT
<213> ORGANISM: artificial
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: X is R, F or P
<220> FEATURE:
<221> NAME/KEY: MISC_FEATURE
<222> LOCATION: (5)..(5)
<223> OTHER INFORMATION: X is F or V
<220> FEATURE:
<221> NAME/KEY: MISC_FEATURE
<222> LOCATION: (10)..(10)
<223> OTHER INFORMATION: X is Q, H or L
<220> FEATURE:
<221> NAME/KEY: MISC_FEATURE
<222> LOCATION: (12)..(12)
<223> OTHER INFORMATION: X is W or G
<220> FEATURE:
<221> NAME/KEY: MISC_FEATURE
<222> LOCATION: (13)..(13)
<223> OTHER INFORMATION: X is A or D

<400> SEQUENCE: 11

Cys Gly Pro Xaa Xaa Met His Gly Leu Xaa Leu Xaa Xaa Asp Glu Gly
1               5                   10                  15

Pro Cys

<210> SEQ ID NO 12
<211> LENGTH: 18
<212> TYPE: PRT
<213> ORGANISM: artificial
<220> FEATURE:
<223> OTHER INFORMATION: synthetic

<400> SEQUENCE: 12

Cys Gly Pro Arg Val Met His Gly Leu His Leu Gly Asp Asp Glu Gly
1               5                   10                  15

Pro Cys

<210> SEQ ID NO 13
<211> LENGTH: 18
<212> TYPE: PRT
<213> ORGANISM: artificial
<220> FEATURE:
<223> OTHER INFORMATION: synthetic

<400> SEQUENCE: 13

Cys Gly Pro Arg Phe Met His Gly Leu Gln Leu Trp Ala Asp Glu Gly
1               5                   10                  15

Pro Cys

<210> SEQ ID NO 14
<211> LENGTH: 18
<212> TYPE: PRT
<213> ORGANISM: artificial
<220> FEATURE:
```

<223> OTHER INFORMATION: synthetic

<400> SEQUENCE: 14

Cys Gly Pro Arg Val Met His Gly Leu Gln Leu Trp Ala Asp Glu Gly
1               5                   10                  15

Pro Cys

<210> SEQ ID NO 15
<211> LENGTH: 18
<212> TYPE: PRT
<213> ORGANISM: artificial
<220> FEATURE:
<223> OTHER INFORMATION: synthetic

<400> SEQUENCE: 15

Cys Gly Pro Arg Val Met His Gly Leu His Leu Trp Asp Asp Glu Gly
1               5                   10                  15

Pro Cys

<210> SEQ ID NO 16
<211> LENGTH: 18
<212> TYPE: PRT
<213> ORGANISM: artificial
<220> FEATURE:
<223> OTHER INFORMATION: synthetic

<400> SEQUENCE: 16

Cys Gly Pro Arg Val Met His Gly Leu Gln Leu Trp Asp Asp Glu Gly
1               5                   10                  15

Pro Cys

<210> SEQ ID NO 17
<211> LENGTH: 18
<212> TYPE: PRT
<213> ORGANISM: artificial
<220> FEATURE:
<223> OTHER INFORMATION: synthetic

<400> SEQUENCE: 17

Cys Gly Pro Arg Val Met His Gly Leu His Leu Trp Ala Asp Glu Gly
1               5                   10                  15

Pro Cys

<210> SEQ ID NO 18
<211> LENGTH: 18
<212> TYPE: PRT
<213> ORGANISM: artificial
<220> FEATURE:
<223> OTHER INFORMATION: synthetic

<400> SEQUENCE: 18

Cys Gly Pro Phe Val Met His Gly Leu His Leu Gly Asp Asp Glu Gly
1               5                   10                  15

Pro Cys

<210> SEQ ID NO 19
<211> LENGTH: 18
<212> TYPE: PRT
<213> ORGANISM: artificial
<220> FEATURE:
<223> OTHER INFORMATION: synthetic

<400> SEQUENCE: 19

Cys Gly Pro Pro Val Met His Gly Leu His Leu Trp Asp Asp Glu Gly

-continued

```
1               5                   10                  15

Pro Cys

<210> SEQ ID NO 20
<211> LENGTH: 18
<212> TYPE: PRT
<213> ORGANISM: artificial
<220> FEATURE:
<223> OTHER INFORMATION: synthetic

<400> SEQUENCE: 20

Cys Gly Pro Arg Val Met His Gly Leu Leu Leu Gly Ala Asp Glu Gly
1               5                   10                  15

Pro Cys

<210> SEQ ID NO 21
<211> LENGTH: 22
<212> TYPE: PRT
<213> ORGANISM: artificial
<220> FEATURE:
<223> OTHER INFORMATION: synthetic
<220> FEATURE:
<221> NAME/KEY: MISC_FEATURE
<222> LOCATION: (8)..(8)
<223> OTHER INFORMATION: X is R, F or P
<220> FEATURE:
<221> NAME/KEY: MISC_FEATURE
<222> LOCATION: (9)..(9)
<223> OTHER INFORMATION: X is F or V
<220> FEATURE:
<221> NAME/KEY: MISC_FEATURE
<222> LOCATION: (14)..(14)
<223> OTHER INFORMATION: X is Q, H or L
<220> FEATURE:
<221> NAME/KEY: MISC_FEATURE
<222> LOCATION: (16)..(16)
<223> OTHER INFORMATION: X is W or G
<220> FEATURE:
<221> NAME/KEY: MISC_FEATURE
<222> LOCATION: (17)..(17)
<223> OTHER INFORMATION: X is A or D

<400> SEQUENCE: 21

Ser Gly Ser Gly Cys Gly Pro Xaa Xaa Met His Gly Leu Xaa Leu Xaa
1               5                   10                  15

Xaa Asp Glu Gly Pro Cys
            20

<210> SEQ ID NO 22
<211> LENGTH: 22
<212> TYPE: PRT
<213> ORGANISM: artificial
<220> FEATURE:
<223> OTHER INFORMATION: synthetic

<400> SEQUENCE: 22

Ser Gly Ser Gly Cys Gly Pro Arg Val Met His Gly Leu His Leu Gly
1               5                   10                  15

Asp Asp Glu Gly Pro Cys
            20
```

```
<210> SEQ ID NO 23
<211> LENGTH: 22
<212> TYPE: PRT
<213> ORGANISM: artificial
<220> FEATURE:
<223> OTHER INFORMATION: synthetic

<400> SEQUENCE: 23

Ser Gly Ser Gly Cys Gly Pro Arg Phe Met His Gly Leu Gln Leu Trp
1               5                   10                  15

Ala Asp Glu Gly Pro Cys
            20

<210> SEQ ID NO 24
<211> LENGTH: 22
<212> TYPE: PRT
<213> ORGANISM: artificial
<220> FEATURE:
<223> OTHER INFORMATION: synthetic

<400> SEQUENCE: 24

Ser Gly Ser Gly Cys Gly Pro Arg Val Met His Gly Leu Gln Leu Trp
1               5                   10                  15

Ala Asp Glu Gly Pro Cys
            20

<210> SEQ ID NO 25
<211> LENGTH: 22
<212> TYPE: PRT
<213> ORGANISM: artificial
<220> FEATURE:
<223> OTHER INFORMATION: synthetic

<400> SEQUENCE: 25

Ser Gly Ser Gly Cys Gly Pro Arg Val Met His Gly Leu His Leu Trp
1               5                   10                  15

Asp Asp Glu Gly Pro Cys
            20

<210> SEQ ID NO 26
<211> LENGTH: 22
<212> TYPE: PRT
<213> ORGANISM: artificial
<220> FEATURE:
<223> OTHER INFORMATION: synthetic

<400> SEQUENCE: 26

Ser Gly Ser Gly Cys Gly Pro Arg Val Met His Gly Leu Gln Leu Trp
1               5                   10                  15

Asp Asp Glu Gly Pro Cys
            20

<210> SEQ ID NO 27
<211> LENGTH: 22
<212> TYPE: PRT
<213> ORGANISM: artificial
<220> FEATURE:
<223> OTHER INFORMATION: polypeptide

<400> SEQUENCE: 27

Ser Gly Ser Gly Cys Gly Pro Arg Val Met His Gly Leu His Leu Trp
1               5                   10                  15

Ala Asp Glu Gly Pro Cys
            20
```

```
<210> SEQ ID NO 28
<211> LENGTH: 22
<212> TYPE: PRT
<213> ORGANISM: artificial
<220> FEATURE:
<223> OTHER INFORMATION: synthetic

<400> SEQUENCE: 28

Ser Gly Ser Gly Cys Gly Pro Phe Val Met His Gly Leu His Leu Gly
1               5                   10                  15

Asp Asp Glu Gly Pro Cys
            20

<210> SEQ ID NO 29
<211> LENGTH: 22
<212> TYPE: PRT
<213> ORGANISM: artificial
<220> FEATURE:
<223> OTHER INFORMATION: synthetic

<400> SEQUENCE: 29

Ser Gly Ser Gly Cys Gly Pro Pro Val Met His Gly Leu His Leu Trp
1               5                   10                  15

Asp Asp Glu Gly Pro Cys
            20

<210> SEQ ID NO 30
<211> LENGTH: 22
<212> TYPE: PRT
<213> ORGANISM: artificial
<220> FEATURE:
<223> OTHER INFORMATION: synthetic

<400> SEQUENCE: 30

Ser Gly Ser Gly Cys Gly Pro Arg Val Met His Gly Leu Leu Leu Gly
1               5                   10                  15

Ala Asp Glu Gly Pro Cys
            20

<210> SEQ ID NO 31
<211> LENGTH: 18
<212> TYPE: DNA
<213> ORGANISM: Artificial Sequence
<220> FEATURE:
<223> OTHER INFORMATION: synthetic

<400> SEQUENCE: 31
attcacctga ctgacgac                                             18

<210> SEQ ID NO 32
<211> LENGTH: 4
<212> TYPE: PRT
<213> ORGANISM: Artificial Sequence
<220> FEATURE:
<223> OTHER INFORMATION: synthetic

<400> SEQUENCE: 32

Ser Gly Ser Gly
1

<210> SEQ ID NO 33
<211> LENGTH: 7
<212> TYPE: PRT
<213> ORGANISM: Artificial Sequence
<220> FEATURE:
<223> OTHER INFORMATION: synthetic
```

```
<400> SEQUENCE: 33

Phe Leu Ile Gly Pro Val Ile
1               5

<210> SEQ ID NO 34
<211> LENGTH: 24
<212> TYPE: PRT
<213> ORGANISM: Artificial Sequence
<220> FEATURE:
<223> OTHER INFORMATION: synthetic

<400> SEQUENCE: 34

Ser Gly Ser Gly Val Asn Val Tyr Ala Val Thr Lys Glu Asn Thr Ile
1               5                   10                  15

Ile Asn Pro Ser Glu Asn Gly Asp
            20

<210> SEQ ID NO 35
<211> LENGTH: 22
<212> TYPE: PRT
<213> ORGANISM: Artificial Sequence
<220> FEATURE:
<223> OTHER INFORMATION: synthetic

<400> SEQUENCE: 35

Ser Gly Ser Gly Cys Gly Pro Asn Asp Ala Asn His Asp Ala Val Asp
1               5                   10                  15

Asn Ala Arg Gly Pro Cys
            20
```